US008105517B2

(12) United States Patent
Suzuki et al.

(10) Patent No.: US 8,105,517 B2
(45) Date of Patent: Jan. 31, 2012

(54) FIGURE-FORMING COMPOSITION, METHOD FOR FORMING THREE-DIMENSIONAL FIGURES AND THREE-DIMENSIONAL STRUCTURES BY USING THE SAME

(75) Inventors: Shigeki Suzuki, Tokyo (JP); Koutaro Shimizu, Tokyo (JP); Shinya Wasada, Tokyo (JP); Hironobu Okamoto, Hyogo (JP); Shinro Takai, Kyoto (JP)

(73) Assignee: Next21 K.K., Tokyo (JP)

(*) Notice: Subject to any disclaimer, the term of this patent is extended or adjusted under 35 U.S.C. 154(b) by 188 days.

(21) Appl. No.: 12/297,854

(22) PCT Filed: Apr. 10, 2007

(86) PCT No.: PCT/JP2007/000382
§ 371 (c)(1),
(2), (4) Date: Apr. 14, 2009

(87) PCT Pub. No.: WO2007/122804
PCT Pub. Date: Nov. 1, 2007

(65) Prior Publication Data
US 2009/0298033 A1   Dec. 3, 2009

(30) Foreign Application Priority Data
Apr. 21, 2006 (JP) .................................. 2006-118584

(51) Int. Cl.
*B29C 67/24* (2006.01)
(52) U.S. Cl. ........ 264/128; 264/112; 264/113; 264/123; 264/340
(58) Field of Classification Search .................. 264/112, 264/113, 123, 128, 340
See application file for complete search history.

(56) References Cited

U.S. PATENT DOCUMENTS

| 5,204,055 A | 4/1993 | Sachs et al. |
| 5,387,380 A * | 2/1995 | Cima et al. ..................... 264/128 |
| 5,437,722 A | 8/1995 | Borenstein |

(Continued)

FOREIGN PATENT DOCUMENTS

EP    1009621    6/2000

(Continued)

OTHER PUBLICATIONS

International Search Report issued Jul. 17, 2007, in International Application No. PCT/JP2007/000382, with English translation (4 pages).

(Continued)

*Primary Examiner* — Joseph Del Sole
*Assistant Examiner* — Timothy Kennedy
(74) *Attorney, Agent, or Firm* — Osha • Liang LLP

(57) ABSTRACT

It is an object of the present invention to provide a figure-forming composition which enables the initiation of hardening even with a small amount of water and can attain a prescribed hardness, and which is suitable particularly for the production of three-dimensional living body models for surgical training by a rapid prototype process; and provide a three dimensional figure and a three-dimensional structure which are formed by using the composition. The figure-forming composition, for example, comprises a calcium-based material such as hemihydrate gypsum and polyvinyl alcohol resin, wherein the content of the polyvinyl alcohol resin is 2 to 20 weight parts when the total weight of the calcium-based material and the polyvinyl alcohol resin is 100 weight parts.

8 Claims, 5 Drawing Sheets

U.S. PATENT DOCUMENTS

| | | | |
|---|---|---|---|
| 5,902,441 | A | 5/1999 | Bredt et al. |
| 6,375,874 | B1 | 4/2002 | Russell et al. |
| 6,403,002 | B1 | 6/2002 | van der Geest |
| 6,416,850 | B1 | 7/2002 | Bredt et al. |
| 6,989,115 | B2 | 1/2006 | Russell et al. |
| 7,037,382 | B2 | 5/2006 | Davidson et al. |
| 7,435,368 | B2 | 10/2008 | Davidson et al. |
| 2001/0050031 | A1 | 12/2001 | Bredt et al. |
| 2002/0029094 | A1 | 3/2002 | Koreishi |
| 2002/0079601 | A1 | 6/2002 | Russell et al. |
| 2003/0030170 | A1* | 2/2003 | Abe et al. ............ 264/113 |
| 2004/0012112 | A1 | 1/2004 | Davidson et al. |
| 2004/0056378 | A1 | 3/2004 | Bredt et al. |
| 2005/0197431 | A1 | 9/2005 | Bredt et al. |
| 2006/0141145 | A1 | 6/2006 | Davidson et al. |
| 2009/0011066 | A1 | 1/2009 | Davidson et al. |

FOREIGN PATENT DOCUMENTS

| | | | |
|---|---|---|---|
| EP | 1542858 | | 6/2005 |
| JP | 63-025021 | | 2/1988 |
| JP | 03-243643 | | 10/1991 |
| JP | 05-319890 | | 12/1993 |
| JP | 08-337459 | | 12/1996 |
| JP | 09-48681 | | 2/1997 |
| JP | 09-124874 | | 5/1997 |
| JP | 10-207194 | | 8/1998 |
| JP | 10-226558 | A2 | 8/1998 |
| JP | 2000-016046 | A2 | 1/2000 |
| JP | 2000-178064 | | 6/2000 |
| JP | 2000-233962 | | 8/2000 |
| JP | 2001-524897 | | 12/2001 |
| JP | 2002-67174 | | 3/2002 |
| JP | 2003-531220 | | 10/2003 |
| JP | 2004-538191 | | 12/2004 |
| JP | 2005-503939 | | 2/2005 |
| JP | 2005-148578 | | 6/2005 |
| JP | 2006-504813 | | 2/2006 |
| WO | 2004/028787 | | 4/2004 |
| WO | 2005/011536 | | 2/2005 |

OTHER PUBLICATIONS

Cement Sekko Sekkai Handbook, edited by The society of Inorganic Materials, Japan; first edition; Gihodo Shuppan, 1995 Nen, pp. 426-427.

Patent Abstracts of Japan, English abstract for JP 63-025021, published Feb. 2, 1088 (2 pages) (Publication not available).

esp@cenet English Abstract for EP-1542858 published Jun. 22, 2005 (1 page).

esp@cenet English Abstract for WO2004-028787 published Apr. 8, 2004 (1 page).

Patent Abstracts of Japan, English Abstract for JP 09-124874, published May 13, 1997 (1 page).

Patent Abstracts of Japan, English abstract for JP03-243643, published Oct. 30, 1991 (1 page).

esp@cenet English abstract for WO2005-011536, published Feb. 10, 2005 (1 page).

Patent Abstracts of Japan, English abstract for JP2005-148578, published Jun. 9, 2005 (1 page).

Patent Abstracts of Japan, English abstract for JP-5319890, published Dec. 3, 1993 (1 page).

esp@cenet English abstract for JP-8337459, published Dec. 24, 1996 (1 page).

Patent Abstracts of Japan, English abstract for JP2000-178064, published Jun. 27, 2000 (1 page).

Patent Abstracts of Japan, English abstract for JP2000-233962, published Aug. 29, 2000 (1 page).

Patent Abstracts of Japan, English Abstract for JP10-226558, published Aug. 25, 1998 (1 page).

Patent Abstracts of Japan, English abstract for JP2000-016046, published Jan. 18, 2000 (1 page).

Patent Abstracts of Japan, English abstract for JP 10-207194, published Aug. 7, 1998 (2 pages).

Patent Abstracts of Japan, English abstract for JP 09-048681, published Feb. 18, 1997 (2 pages).

* cited by examiner

Fig. 4
Fig. 4(a)
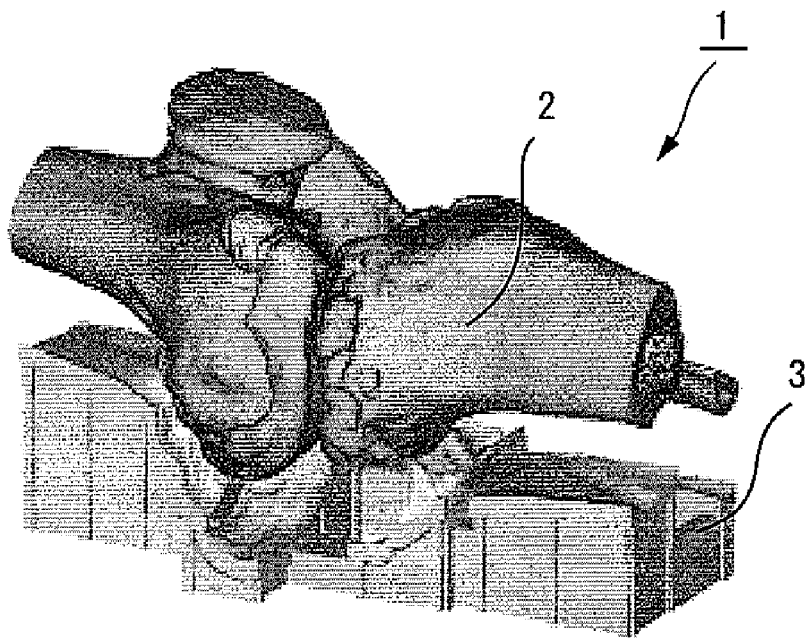
Fig. 4(b)
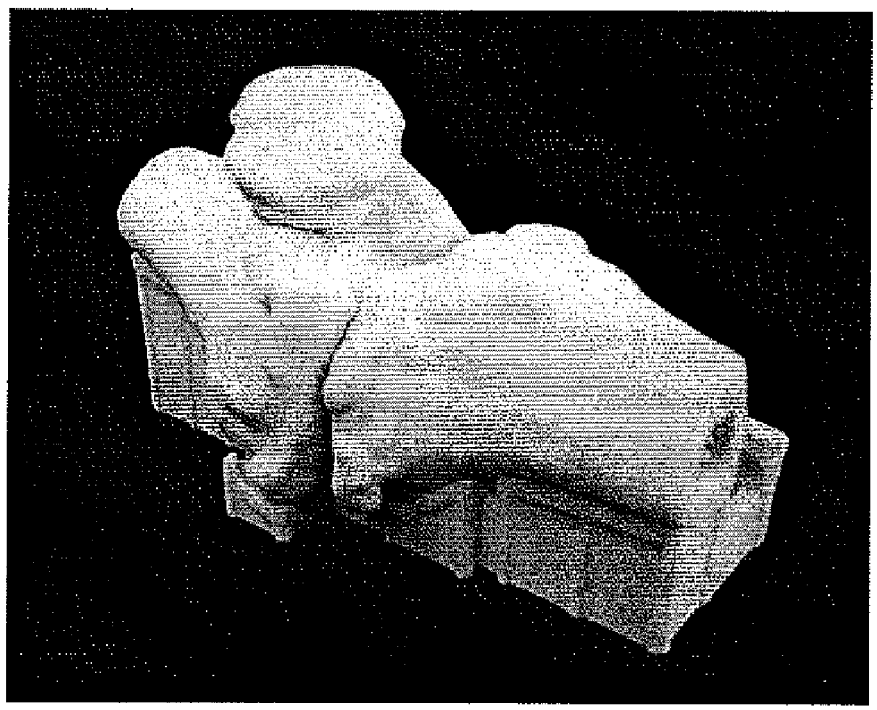

Fig. 5
Fig. 5(a)
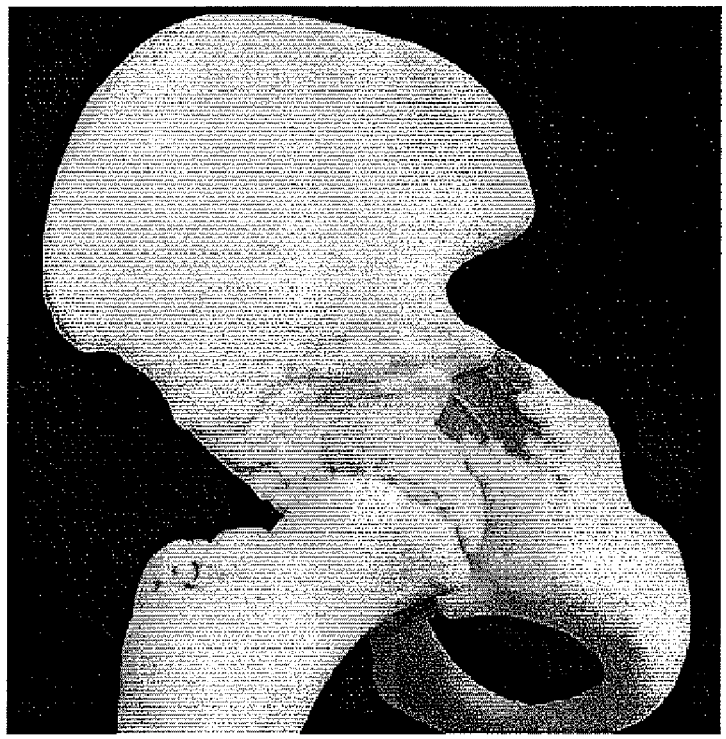
Fig. 5(b)
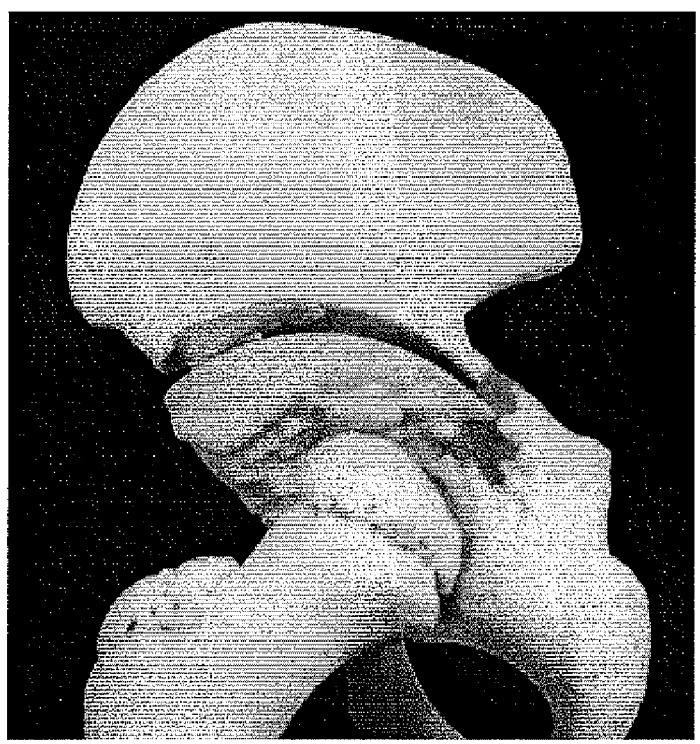

FIGURE-FORMING COMPOSITION, METHOD FOR FORMING THREE-DIMENSIONAL FIGURES AND THREE-DIMENSIONAL STRUCTURES BY USING THE SAME

BACKGROUND OF THE INVENTION

1. Field of the Invention

The present invention relates to a figure-forming composition, a production process of three-dimensional figures or structures, and three-dimensional living body models. In particular, the present invention relates to a figure-forming composition having characteristics of attaining a prescribed hardness with a small amount of water by basically containing a relatively large amount of polyvinyl alcohol resin (and hardening accelerator). The present invention also relates to a method for obtaining three-dimensional structures having desired hardness by adding enough water (preferably water and cross-linker) to sophisticated three-dimensional figures which is rapidly formed by accumulating a plurality of layers patterned with a little moisture by using the figure-forming composition. The present invention further relates to a technique of producing custom-made three-dimensional living body models by using the method for producing three-dimensional structures.

2. Description of the Related Art

In the orthopedic medical field, for example, there is a demand for surgery training using three-dimensional living body models such as bone parts. There is also a demand for having a concrete image of a surgery beforehand to prepare for a real surgery by using a three-dimensional model of a part including a diseased site of a patient. However, it was difficult to obtain custom made three-dimensional living body models. In addition, three-dimensional living body models contain wax which leaks out when sterilization procedure was performed to the models. So, the models can not be used in operating rooms.

In recent years, rapid prototyping apparatus for easily forming three-dimensional structures (shown in, for example JP-T 2001-524897, JP-T 2003-531220, JP-T 2004-538191, JP-T 2005-503939, U.S. Pat. No. 5,204,055 specification, U.S. Pat. No. 5,340,656 specification, U.S. Pat. No. 5,387,380 specification, U.S. Pat. No. 6,007,318 specification, U.S. Pat. No. 6,375,874 specification, U.S. Pat. No. 5,902,441 specification and U.S. Pat. No. 6,416,850 specification. These are incorporated herein for reference purposes) and rapid prototype process are increasingly used. Three dimensional objects, such as prototype parts of apparatus, are used to examine the performance thereof. The prototype parts have been produced by injection molding. Compared with a conventional method such as injection molding, the rapid prototype process has greater advantage in terms of time and cost. The examples of rapid prototype method include stereolithography method, powder sintering method, powder binding method, and solid ground curing technology (SGC), which forms thin layers based on a cross sectional shape data to form three-dimension shape by laminating the thin layers.

Stereolithography is a method for forming three-dimensional shape by laminating thin layers by repeating the following processes: solidifying thin layers by irradiating laser beam to liquid light curing resin accommodated in a container based on cross-sectional shape data of three-dimensional objects to be formed, followed by pouring the same liquid light curing resin on the thin film and irradiating laser beam thereto. However, the light curing resin is difficult to handle because it is highly photoreactive and also it is in a liquid state. There is also a problem that the accuracy of formed objects is not always high because the resin shrinks when it is hardened.

The powder sintering method laminates thin layers which are formed from powders, instead of light curing resin used in stereolithography, by sintering powders with laser beam irradiation. With this method, three-dimensional structures can be formed with metals and ceramics. However, there are problems that high-power laser must be used to sinter powders and the optical control is difficult.

In the powder binding method, powder materials are used as well. But in contrast to the powder sintering method, thin layers are accumulated and solidified by using adhesive agent. With this method, three-dimensional structures can be formed relatively quickly. But, since this method uses adhesive agent to bind powder materials, the resultant structures do not have enough hardness. This method also has a problem that the layer structure is not continuous because layers are bound together with adhesive agent.

Solid ground curing technology (SGC) is as follows. Firstly, a mask pattern is formed based on cross-sectional shape data and ultraviolet irradiation is performed on this mask pattern which is accumulated on a resin layer on which light curing resin is applied. Having performed enough ultraviolet radiation, unhardened ultraviolet resin layer is removed, and heat-hardening resin is filled in the depressed area which is formed by removing the unhardened ultraviolet resin layer. Then, the filled heat-hardening resin is hardened, a thin layer composed of hardened ultraviolet hardening resin and hardened heat-hardening resin is formed. Having this thin layer laminated into a three-dimensional structure, ultraviolet hardening resin is dissolved. With this technology, there is a problem of noise when the unhardened ultraviolet resin layer is removed by suction. There is further a problem that highly qualified three-dimensional shape cannot be obtained.

Japanese Patent Laid-Open No. 10-207194 discloses a laminate molding method for molding three-dimensional objects by laminating thin layers which is formed from powder material in a sheet shape. It shows "a laminate molding method for forming three-dimensional objects comprising the steps of: forming electrostatic latent image on the surface of a dielectric, based on arbitrary cross-sectional shape data of a three-dimensional object; developing the electrostatic latent image with electrifiable powder; forming the electrifiable powder in a sheet shape; and copying the sheet-like electrifiable powder on a stage. By repeatedly performing the above steps, sheet-shaped electrifiable powder material is laminated and a three-dimensional object is molded."

However, in the method for molding three-dimensional objects, disclosed in the Japanese Patent Laid-Open No. 10-207194, basically, thin layers of electrifiable powder material are formed and laminated to form three-dimensional structures by using electrophotographic photoreceptor drum. So, the method is not suitable for forming three-dimensional structures using materials like gypsum.

Japanese Patent Laid-Open No. 2002-67174 discloses a data processing apparatus for generating molding data to be used in three-dimensional molding, "which comprises: a shape data inputting means for inputting shape data regarding shape of an object; a feel information acquiring means for acquiring feel information regarding texture of the object; and a data generating means for generating the molding data for duplicating the shape and feel of the object on the basis of the shape data and the feel information." This apparatus is considered to be able to duplicate the feel of objects precisely.

The Japanese Patent Laid-Open No. 2002-67174 discloses a rapid prototyping apparatus used for powder molding method and powder sintering method. But an apparatus using gypsum in particular is not disclosed.

Japanese Patent Laid-Open No. 2005-148578 discloses a technology for producing rigid three-dimensional model in which layers of gypsum powder are obtained based on layer data of objects, and the layers are laminated by being fixed with binders (see paragraph [0008] and [0026] of the bulletin).

However, the technology disclosed in the Japanese Patent Laid-Open No. 2005-148578 is mainly related to producing three-dimensional models of organs which characterizes to soften the rigid three-dimensional model obtained by laminating materials such as gypsum. (see, for example, claim 14 and paragraph [0022] to [0034]). So, the process of producing rigid three-dimensional models from gypsum powder is not described in detail. Also, since it is aimed at producing three-dimensional model of organs, which does not have hardness like that of bones, the resultant three-dimensional models are not always suitable for surgical training. Furthermore, the resultant three-dimensional models are not intended to go through autoclave treatment, and so the models are generally soaked in wax, or the binders contained includes wax ingredient. As a result, when the three-dimensional model is heated in an autoclave, wax ingredient elutes therefrom, and the form and the hardness thereof changes.

On the other hand, gypsum is widely used for building material and three-dimensional models. For example, Japanese Patent Laid-Open No. 63-25021 discloses a technology for mixing polyvinyl alcohol fiber in hemihydrate gypsum (see line 9 to 16 upper left). But, the polyvinyl alcohol fiber is cited only as an example of ingredient mixed in gypsum to prevent a gypsum mold from cracking.

In the field of building material, it is known that polyvinyl alcohol resin is mixed with hemihydrate gypsum in order to raise the hardness of gypsum compact. For example, JP-A 05-319890, JP-A 08-337459, JP-A 09-48681, and JP-A 2000-178064 discloses inventions using gypsum and polyvinyl alcohol resin.

The JP-A 05-319890 discloses "a gypsum composition prepared by mixing powders of polyvinyl alcohol based polymer, 90% of which is dissolved in water at 80 degrees Celsius for 20 minutes (A) and powders which can thicken the polyvinyl alcohol based polymer (B) with powders mainly containing hemihydrate gypsum (C)". In the embodiment of JP-A 05-319890, 100 weight parts of hemihydrate gypsum is mixed with 1 part by weight of carboxyl group modified polyvinyl alcohol, with polymerization degree of 1750, saponification degree of 98 mol %, particle size of 30 mesh path, which is 2 mol % maleic acid copolymerized. However, since the content of polyvinyl alcohol resin is small, enough hardness can not always be obtained with a little amount of water. But in JP-A 05-319890, since the gypsum composition is intended to be used in the form of slurry, there is no problem even if the content of polyvinyl alcohol resin is small.

The JP-A 08-337459 discloses "gypsum composition which can be hardened and forms a water-resistant gypsum product by hydration, comprising a mixture of: a) 100 weight parts of gypsum, and b) 0.5 to 20 weight parts of aqueous emulsion solids, per 100 weight parts of gypsum, wherein the aqueous emulsion comprising water and: i) a paraffin hydrocarbon having a melting point of 40 to 80° C.; ii) montan wax in an amount of about 1 to 200 weight parts, per 100 weight parts of the paraffin hydrocarbon, and iii) polyvinyl alcohol in an amount of about 1 to 50 weight parts, per 100 weight parts of the paraffin hydrocarbon." (see claim 4 of the bulletin) However, since the gypsum composition contains paraffin wax, when the molding is placed in an autoclave, wax ingredient elutes therefrom, and the form and the hardness thereof changes.

The JP-A 09-48681 discloses "gypsum hardened body whose surface is coated with acrylic emulsion, vinyl acetate emulsion or polyvinyl alcohol coating material". In the bulletin, polyvinyl alcohol coating material is disclosed as material applied on the surface of gypsum hardened body.

The above JP-A 2000-178064 discloses "gypsum hardened body comprising gypsum, polyvinyl alcohol resin, and fluorinated compound" (see claim 1 of the bulletin). It is preferred that "1 to 30 weight parts of polyvinyl alcohol resin (further preferred 5 to 20 weight parts) is included, per 100 weight parts of gypsum" (see paragraph [0009] of the bulletin). However, the gypsum hardened body disclosed in the bulletin contains fluorinated compound as an essential element, and as disclosed in paragraph [0011], it is intended to be mixed with water.

JP-T 2003-531220 discloses a composition for three-dimensional printing of solid objects. However, it does not particularly use calcium-based material nor polyvinyl alcohol derivatives. So, it was difficult to obtain sophisticated three-dimensional figures by RP process in a short period.

JP-T 2001-524897 discloses a method for producing molded bodies which is formed from powder material by repeating the steps of: forming a layer of powder material, applying powder material in water pattern, and forming a layer of powder material combined in pattern (see claim 1 of the patent). And in the embodiment, polyvinyl alcohol itself was used as powder material, and a molded body was obtained. (see page 9 of the bulletin). However, when only polyvinyl alcohol is used, it is difficult to obtain molded bodies by PR process.

The object of the present invention is to provide a figure-forming composition which initiates hardening even with a small amount of water, and can attain a prescribed hardness, and which is suitable particularly for producing three-dimensional living body models for surgery training by a rapid prototype process.

The object of the present invention is to obtain three-dimensional figures which are for example tentative structures to obtain three-dimensional structure living body models such as three-dimensional living body models, implants or artificial bones by using the above figure-forming composition.

The object of the present invention is to obtain three-dimensional structures such as three-dimensional living body models, implants or artificial bones. In particular, it is an object of the present invention to obtain three-dimensional structures, which is relatively uniform and sophisticated, and are not be deformed in high temperatures in an autoclave and the like.

The object of the present invention is to provide custom made three-dimensional living body models which can be used for surgical training, explanations of surgical planning, and explanations of bone or tooth site of patients' in front of the patients, and implants and artificial bones having desired shapes to be embedded.

SUMMARY OF THE INVENTION

The present invention is basically based on the following idea. A figure-forming composition such as gypsum composition having sufficient characteristics of attaining prescribed hardness with a small amount of water by basically containing relatively a large amount of polyvinyl alcohol resin (and hardening accelerator), which is particularly suitable for rapid prototype processing, can be obtained. It is also based on the following idea. Three-dimensional structures such as gypsum hardened body having desirable hardness can be obtained by adding enough water (preferably water and cross-linker) to sophisticated three-dimensional figures which was rapidly formed by accumulating a plurality of layers patterned with a little water by using the figure-forming composition. In this way, custom made three-dimensional living body models, implants, artificial bones, or the like can be produced.

The figure-forming composition according to the first aspect of the present invention is a figure-forming composition comprising a calcium-based material and a polyvinyl alcohol resin, wherein the polyvinyl alcohol resin is 2 to 8 weight parts when the total weight of the calcium-based material and the polyvinyl alcohol resin is 100 weight parts. The figure-forming composition of the present invention is preferred to be composed mostly of calcium-based material.

In this specification, "figure-forming composition" is a composition containing calcium-based material which has not been hardened and is a former state of a molded body. Specific examples of calcium-based material include one kind or a mixture of more than one kind of: gypsum such as hemihydrate gypsum; or calcium phosphate-based substance such as hydroxyapatite, carbonate apatite, fluorapatite, chlorapatite, β-TCP, α-TCP, calcium metaphosphate, tetra-calcium phosphate, calcium hydrogen phosphate, calcium dihydrogen phosphate, and calcium pyrophosphate, calcium carbonate, calcium sulfate, the salt thereof or the solvate thereof. Among them, gypsum is preferred. In particular, as demonstrated in the example described below, hemihydrate gypsum is preferred. But, instead of gypsum or together with gypsum, calcium phosphate-based substance may be included as appropriate. Calcium phosphate-based substance may be used as fillers. Calcium phosphate-based substance such as hydroxyapatite can be used in the same way as gypsum because it absorbs water like gypsum does. Furthermore, it is preferred because the resultant three-dimensional structures can be used as implants or artificial bones.

In this specification, "hemihydrate gypsum" is a compound which basically has trigonal system shown by a composition formula $(CaSO_4 \cdot \frac{1}{2}H_2O)$. It is classified into a type or β type, and the classification can be easily made by using powder X-rays method, capillary analysis method, Hanawalt method as appropriate. Also, since the specific gravity is around 2.76 and 2.64 respectively, the classification can be made by measuring the specific gravity. In the present invention, although a type hemihydrate gypsum, β type hemihydrate gypsum, or the mixture of both can be used as appropriate, but, as described below, a type hemihydrate gypsum is preferred.

When figure-forming composition containing gypsum and polyvinyl alcohol resin is used for building material, polyvinyl alcohol resin is mixed with the figure-forming composition which is made in the form of slurry by mixing gypsum and water. Then, the figure-forming composition in the form of slurry is charged in a mold or is painted on a wall. In so doing, bubbles are generated when the content of polyvinyl alcohol resin exceeds 1 part by weight. So, there is a problem that when figure-forming composition having bubbles are used, molding is difficult and the resultant molded body is fragile. Therefore, the content of polyvinyl alcohol is generally equal to or less than 1 part by weight. The figure-forming composition of the present invention actually does not include water except for crystal water (for example, the water content is less than 1 part by weight, preferably less than 0.5 weight parts, further preferably zero content). So, bubbles can be prevented from being generated even though relatively large amount of polyvinyl alcohol resin is mixed. Since relatively large amount of polyvinyl alcohol is mixed, the figure-forming composition of the present invention can attain a prescribed hardness in a short period and maintain high level of hardness even when it is hydration hardened with a little amount of water.

The figure-forming composition of the present invention can be preferably used for forming three-dimensional figures such as three-dimensional living body models, implants or artificial bones. In particular, a figure-forming composition which is preferably used for a method for producing three-dimensional structures can be provided by repeating the steps of: layering powdered three-dimensional structures; and forming hardened parts by adding water or binder aqueous solution to the part to be hardened. In this way, since the figure-forming composition is not need to be mixed with water, bubbles are not generated even when a relatively large amount of polyvinyl alcohol resin is mixed with the figure-forming composition. Consequently, the figure-forming composition can be preferably utilized. Also, the figure-forming composition of the present invention is preferred to be hardened relatively in a short period, because the figure-forming composition of the present invention is formed by layering hardened figure-forming composition one after another. On the other hand, the figure-forming composition of the present invention does not need to have enough fluidity of building material. As a result, by preparing the figure-forming composition substantially without water, and adding minimum amount of water for hardening figure-forming composition, hardening reaction can be caused and hardening can be achieved in a short period. As a result, three-dimensional molded bodies (three-dimensional figures) formed from multiple layers of hardened material can be effectively produced by using the figure-forming composition. In addition, since the figure-forming composition contains relatively large amount of polyvinyl alcohol resin (even if gypsum is incompletely hardened), three-dimensional figures having enough hardness for maintaining tentative form can be obtained. And, having formed a three-dimensional figure having the tentative hardness, a three-dimensional structure having proper hardness can be obtained by adding enough water which promotes hardening of gypsum.

A preferred embodiment of the figure-forming composition according to the first aspect of the present invention is a figure-forming composition comprising a calcium-based material, a polyvinyl alcohol resin, and a hardening accelerator, wherein the hardening accelerator is one or more kinds of hardening accelerators selected from the group consisting of "dihydrate gypsum, alkali metal sulfate, alkaline earth metal sulfate, alkali metal chloride salt, alkaline earth metal chloride salt, inorganic acid ammonium salt, and alums", wherein the polyvinyl alcohol resin is 2 to 8 weight parts and the hardening accelerator is 0.1 to 5 weight parts when the total weight of the calcium-based material and the polyvinyl alcohol resin is 100 weight parts.

In this way, the figure-forming composition can be hardened in a short period by adding hardening accelerator thereto. A preferred embodiment of the figure-forming composition of the present invention is to produce three-dimensional models. It is also obtaining three-dimensional structures by repeating a step of forming hardened parts of gypsum by adding water to the part to be hardened. As a result, the hardness thereof may be temporarily inferior to that of ordinary building material. Also, the figure-forming composition need to be hardened relatively quickly, because the figure-forming composition of the present invention is formed by layering hardened figure-forming composition one after another. On the other hand, the figure-forming composition does not need to have enough fluidity of building material. As a result, by preparing the figure-forming composition substantially without water, and adding minimum amount of water for hardening figure-forming composition, hardening reaction can be caused and rapid hardening can be achieved. As a result, three-dimensional molded bodies (three-dimensional figures) formed from multiple layers of gypsum can be effectively produced by using the figure-forming composition. Furthermore, since the figure-forming composition of the present invention is to be formed with a plurality of layers one after another, it is desired that the figure-forming composition become a molded body (three-dimensional figures) with a certain level of hardness relatively quickly. By mixing the above hardening accelerator, the hardening rate of the figure-forming composition can be increased, and a gypsum molded body (three-dimensional figures) having a prescribed hardness can be obtained in a short period.

A preferred embodiment of the figure-forming composition according to the first aspect of the present invention is one of the above described figure-forming composition, wherein the hemihydrate gypsum is α type hemihydrate gypsum.

A preferred embodiment of the figure-forming composition according to the first aspect of the present invention is one of the above described figure-forming composition, wherein the polymerization degree of the polyvinyl alcohol resin is in the range of $2\times10^2$ to $3\times10^3$ both inclusive. If the average polymerization degree of polyvinyl alcohol resin is below $2\times10^2$, the viscosity of slurry becomes too low. In contrast, if the average polymerization degree of polyvinyl alcohol resin is over $3\times10^3$, the viscosity of slurry becomes too high, which makes it difficult to be dissolved in water. So, the range of $2\times10^2$ to $3\times10^3$ is preferred as polymerization degree, and it may also be $5\times10^2$ to $2.5\times10^3$. It may also be $3\times10^3$ to $1\times10^4$, because the figure-forming composition of the present invention is not needed to be placed in a mold nor kneaded. Also, if the polymerization degree is low, when water is added to the figure-forming composition to be in the form of slurry, gypsum particles are settled out therein. But the figure-forming composition of the present invention is not need to be made in the form of slurry. And also it is preferred that the polymerization degree thereof be low, thereby the figure-forming composition easily being dissolved in a little amount of water. So, the range of preferred polymerization degree is, for example, $5\times10$ to $1.9\times10^2$, and it may also be $1\times10^2$ to $1.5\times10^2$.

A preferred embodiment of the figure-forming composition according to the first aspect of the present invention is one of the above described figure-forming composition, wherein the saponification degree of the polyvinyl alcohol resin is equal to or more than 70 mol %. If the saponification degree is less than 70 mol %, the mechanical strength of three-dimensional figures will not be improved. So, the saponification degree is preferred to be equal to or more than 70 mol %, and it is further preferred to be in the range of 80 mol % to 99.5 mol %. (In this specification, A to B means A to B both inclusive.)

A preferred embodiment of the figure-forming composition according to the first aspect of the present invention is one of the above described figure-forming composition, wherein the polyvinyl alcohol resin includes polyvinyl alcohol modified resin, the polyvinyl alcohol modified resin having one or more than one of functional groups selected from the group consisting of "an acetoacetyl group, a silyl group, a quaternary ammonium base, a carboxylic acid group, a carboxylic inorganic base, a sulfonic group, an inorganic base of the sulfonic acid, a ketone group, a mercapto group, and an amino group".

A preferred embodiment of the figure-forming composition according to the first aspect of the present invention is one of the above described figure-forming compositions, wherein the polyvinyl alcohol resin comprises polyvinyl alcohol modified resin having an acetoacetyl group. When polyvinyl alcohol resin having an acetoacetyl group as a functional group is used to produce a figure-forming composition, chelate structure is formed in the figure-forming composition. So, the figure-forming composition will be hardened relatively quickly.

A method for forming three-dimensional figures according to the second aspect of the present invention basically uses one of the above figure-forming compositions which are powder formed in the course of forming three-dimensional figures by rapid prototype process (RP process). By using the above described figure-forming composition, even if a three-dimensional figure is formed by layering multiple layers to which a little amount of water was added, a three-dimensional figure having enough hardness to maintain a tentative form can be formed in a short period.

In particular, a method for forming three-dimensional figures according to the second aspect of the present invention is a method for forming a three-dimensional figure duplicating the shape of an object, the method comprising: a cross-sectional shape obtaining step (step A1) for obtaining information on the cross-sectional shape of each layer by dividing three-dimensional shape of the object into multiple layers; a first cross-sectional figure forming step (step A2-1) comprising the steps of: reading out information on the cross-sectional shape of a first layer from the information on the cross-sectional shape obtained in the cross-sectional shape obtaining step; and forming the first cross-sectional figure duplicating the cross-sectional shape by using a figure-forming composition based on the read out information; a second cross-sectional figure forming step (step A2-2) comprising the steps of: reading out information on the cross-sectional shape of a second layer from the information on the cross-sectional shape obtained in the cross-sectional shape obtaining step, the second layer being located on the upper layer of the first cross-sectional figure; and forming the second cross-sectional figure so as to be overlapped with the first cross-sectional figure, the second cross-sectional figure duplicating the cross-sectional shape from a figure-forming composition based on the read out information; a three-dimensional figure obtaining step (step A2-n) for obtaining the three-dimensional figure duplicating the shape of the object, wherein the three-dimensional figure obtaining step repeats, an upper layer cross-sectional figure forming step for forming an upper layer cross-sectional figure, in the same way as the second cross-sectional figure forming step, reading out information on the cross-sectional shape of the layer to be formed from the information on the cross-sectional shape obtained in the cross-sectional shape obtaining step; and forming the cross-sectional figure of the layer so as to be overlapped with the cross-sectional figure obtained in the former cross-sectional figure forming step, the cross-sectional figure of the layer duplicating the cross-sectional shape from a figure-forming composition based on the read out information, wherein at least one or more of the cross-sectional figure forming steps (preferably all the steps) comprise: a figure-forming composition layer obtaining step for forming figure-forming composition layers by stratifying powders of the figure-forming composition above described; and a water adding step for moistening a predetermined part of the figure-forming composition layer by adding water (preferably, binder aqueous solution or cross-linker solution) to the figure-forming composition layer based on information on the cross-sectional shape of the layer, the layer formed in the figure-forming composition layer obtaining step. Note that as a figure-forming composition, the ones described in this specification can be used as appropriate. In this way, by adding water in a prescribed pattern, the hydration reaction is promoted in the part corresponding to the added pattern. As a result, a patterned hardened object can be obtained.

In this specification, "three-dimensional figure" means a figure which is for example made from gypsum, duplicating the shape of an object through promoting hydration reaction by adding water, binder aqueous solution, cross-linker solution, and the like, to figure-forming composition, and maintaining certain hardness for at least a certain period of time. In this specification, "three-dimensional figure" particularly includes combinations of plural layers which are in a state before forming the final three-dimensional structures, such as gypsum whose hydration reaction is not completed. But "three-dimensional figure" of this specification is not specifically limited to ones whose hydration reaction is not completed, and includes ones which have not hydrated completely when it is formed, but are hydrated by absorbing moisture in the air.

A preferred embodiment of the method for forming three-dimensional figures according to the second aspect of the present invention is the above described method for forming three-dimensional figures, wherein the information on the cross-sectional shape of each layer comprises color identification information of each layer, and wherein water including coloring component is added based on the color identification information in the water adding step.

The three-dimensional model of the present invention is used, for example, as three-dimensional living body models for surgery training. Ordinary models are colored only on the surface thereof, and are not colored inside of models. But, it is not suitable for surgical or dental training, if the color of gypsum appears immediately when bone or tooth is cut off, or if the bone or tooth part cannot be distinguished from flesh part. So, in the method for forming three-dimensional figures according to this embodiment, bone or tooth part and flesh part are colored so that each part can be distinguished from each other. This coloration patterning can be easily made by the method for forming three-dimensional figure of the present invention, because it is not a method for obtaining figures by pouring gypsum in a predetermined mold which is applied in the ordinary method for forming three-dimensional figures. In particular, since the X-ray photograph of bone or tooth part, and that of flesh part (or nervous part) are different in density, when information on cross-sectional shape of each layer is obtained from an X-ray photograph, information of bone or tooth part, and that of flesh part (or nervous part) are stored in different patterns. And then water (e.g. or water containing white colorant) is added to the bone or tooth part, on the other hand water containing predetermined colorant (for example, red colorant) is added to the flesh part. This pattering can be easily performed by well-known printing technique.

The method for forming three-dimensional structures according to the third aspect of the present invention relates to a method for forming three-dimensional structures forming three-dimensional living body models and three-dimensional hardening bodies such as implants or artificial bones, by basically using the above described figure-forming compositions, and three-dimensional figures obtained by the above described method for forming three-dimensional figures. And since hardening bodies are obtained by using a prescribed figure-forming composition as above described, living body models particularly for surgical training can be obtained properly in a short period. The ordinary PR process was not aimed at producing implants or artificial bones. And even if implants or artificial bones are produced by the ordinary RP process, since they include wax and the like, sterilization process can not be performed. So, they can not be used for surgical operation and the like. On the other hand, in the method for forming three-dimensional structures of the present invention, since a prescribed composition was used in forming the structures, implants or artificial bones with sufficient hardness can be obtained without containing wax, and the resultant three-dimensional structures can stand autoclave fertilization.

"Three-dimensional structure" of this specification means hardened materials duplicating the shapes of objects. In particular, it includes three-dimensional models such as living body models, artificial bones incorporated in a living body replacing real bones, implants and the like.

More specifically, the method for forming three-dimensional structures according to the third aspect of the present invention comprises: a gypsum powder removing step (step B1) for removing unconsolidated figure-forming composition powder from the three-dimensional figure obtained by the method for forming a three-dimensional figure as claimed in claim 10; a water adding step (step B2) for adding water to the three-dimensional figure whose unconsolidated powders was removed in the gypsum powder removing step; and a drying step (step B3) for drying the three-dimensional figure to which water was added in the water adding step.

A three-dimensional figure obtained by the above described method for forming three-dimensional figures is formed by adding water to a figure-forming composition by basically using printing techniques. So, it is highly likely that gypsum and the like has not sufficiently hardened by hydration. So, having removed powders which remain on unharden parts unrelated to the shape of the object to be formed, hardening reaction of gypsum and the like by hydration is promoted. In this way, the hardening reaction of gypsum and the like is promoted, and more homogeneous hardened bodies having sufficient hardness can be obtained. As a matter of course, it is desired that three-dimensional figures with water added be dried in a drying step. On the other hand, a method for obtaining hardened bodies by impregnating resultant three-dimensional figures with wax is conceivable. But a hardened body having wax impregnated has a problem that wax leaks out from the body when autoclave sterilization or steam sterilization is performed thereon. Since high temperature sterilization process can not be performed on the bodies, they can not be brought into operating rooms. On the other hand, in the method for forming three-dimensional structures of the present invention, three-dimensional figures are not always needed to be impregnated with wax. So, three-dimensional structures obtained does not have the above problem.

A preferred embodiment of the method for forming three-dimensional structures according to the third aspect of the present invention is one of the above described method for forming a three-dimensional structure comprising the water adding step (step B2) which includes: an atomizing step (step B2-1) for attaching water on the surface of the three-dimensional figure by misting water or by exposing the three-dimensional figure to high humidity atmosphere, the three-dimensional figure being removed unconsolidated powders therefrom in the gypsum powder removing step; and a soaking step (step B2-2) for soaking the three-dimensional figure in water or aqueous solution after the atomizing step. "High humidity atmosphere" referred herein means a condition wherein humidity is the range of 80 to 100% (preferably 90 to 100%). The high humidity atmosphere can be achieved by putting water, cross-linker solution, or binder aqueous solution in a humidifier and the like, and then filling a container or a closed system with moisture vapor, mist or vapor containing a predetermined component.

Namely, in the method for forming three-dimensional structures according to this embodiment, a problem of deformation caused by soaking resultant three-dimensional figures in water suddenly is taken into account. In order to prevent the problem of deformation, moisture is added on the surface of the resultant three-dimensional figures (preferably on all over the surface thereof), thereby promoting hardening reaction of gypsum by hydration preferably, by drying). And then, hardening reaction is further promoted by soaking the three-dimensional figures in water.

A preferred embodiment of the method for forming three-dimensional structures according to the third aspect of the present invention is the above described method for forming three-dimensional structures comprising the water adding step (step B2) which includes one of the following steps: (1) an atomizing step for attaching water on the surface of the three-dimensional figure by misting water or by exposing the three-dimensional figure to high humidity atmosphere, the three-dimensional figure being removed unconsolidated powders therefrom in the gypsum powder removing step, and a soaking step for soaking the three-dimensional figure in cross-linker solution after the atomizing step; (2) an atomizing step for attaching cross-linker solution on the surface of the three-dimensional figure by misting cross-linker solution or by exposing the three-dimensional figure to high humidity atmosphere of cross-linker solution, the three-dimensional figure being removed unconsolidated powders therefrom in the gypsum powder removing step, and a soaking step for soaking the three-dimensional figure in water or cross-linker solution after the atomizing step; or (3) an atomizing step for attaching water on the surface of the three-dimensional figure by misting water or by exposing the three-dimensional figure to high humidity atmosphere, the three-dimensional figure being removed unconsolidated powders therefrom in the gypsum powder removing step, and a soaking step for soaking the three-dimensional figure in water and then in cross-linker solution after the atomizing step.

By adding cross-linker solution in this way, bridging is promoted, thereby obtaining three-dimensional structures having sufficient hardness. The cross-linker solution may be ethylenediamine aqueous solution or ethylenediamine aqueous solution. It may also be aqueous solution of ethylenediamine and the diethanolamine.

The three-dimensional structures according to the fourth aspect of the present invention relates to three-dimensional living body models of parts including patient's bones and teeth, implants, or artificial bones. The ordinary shaped living body models are produced commercially, and they are seen in science laboratory rooms in school facilities. However, ordinary living body models are not always suitable for surgical training, explanation of surgery planning, nor explanation of parts including patient's bones and teeth in front of patients. Also, three-dimensional living body models including patient's bones and teeth, implants, and artificial bones are not need to be mass-produced. So, the object of the present invention is to provide custom made three-dimensional living body models which can be used for surgical training, explanation of surgery planning, and explanation of parts including patient's bones and teeth in front of patients.

In particular, the three-dimensional structures according to the fourth aspect of the present invention relates to a three-dimensional structures including patient's bones or teeth, produced by one of the above described method for forming three-dimensional structures, wherein the shape of the above described object is that of a part including patient's bones or teeth. In this way, custom made three-dimensional structures can be formed easily without using expensive devices such as molds. And, since the resultant three-dimensional living body model duplicates the part including patient's bones and teeth, lines along which a bone is cut can be easily designed, or simulation for moving a bone can easily be performed. Also, a simulation for embedding implants or plates can easily be performed. As a matter of course, since doctors and the like can actually see the three-dimensional living body models, they can understand the part where an operation is performed before the operation. Also, since doctors can explain specific operational sequence to patients before operations, patients can understand the operational sequence which makes them feel secure. Furthermore, existing models including wax ingredient and the like can not be sterilized in autoclave or in high temperature, so they can not be brought in operating rooms. But since the preferred embodiment of three-dimensional living body model of the present invention does not include wax ingredient, it can be sterilized in autoclave or in high temperature, and can be brought in operating rooms. This makes doctors and the like remind of simulated operations previously preformed. Since the objects to be embedded in a living body such as implants or artificial bones obtained in the above way have desirable shapes, they can be preferably used in dentistry or surgical treatment.

The present invention can provide figure-forming composition which is hardened with a little amount of water and attain prescribed hardness because it includes calcium-based material and polyvinyl alcohol resin (or further include hardening accelerator), and which is suitable for forming three-dimensional models particularly by the rapid prototype process (the RP process).

In the present invention, a three-dimensional figure, which is a tentative structure for forming a three-dimensional living body model, can be obtained by using the above described figure-forming composition and the PR process.

In the present invention, gypsum hardened body, which is a three-dimensional living body model for surgical training, can be obtained by using the above described figure-forming composition and three-dimensional figures. In particular, in the present invention, gypsum hardened body with relatively uniform and accurate quality can be obtained by sufficiently hydrating gypsum which is contained in a three-dimensional figure. Also, a gypsum hardened body which will not be deformed in high temperature environment of autoclave can be obtained, because it does not contain wax.

In the present invention, three-dimensional structures (preferably custom made) can be provided. They can be used for surgical training, explanation of surgery planning, and explanation of parts including patient's bones and teeth in front of patients. They can also be brought in operating rooms.

BRIEF DESCRIPTION OF THE DRAWINGS

FIG. 4 shows figures for explaining three-dimensional structures of a join part produced in example 5. FIG. 4(a) is a 3D CG image of an object to be obtained. FIG. 4(b) is a photograph, in place of a diagram, showing three-dimensional structures obtained.

FIG. 5 shows photographs, in place of a diagram, showing a living body model formed in example 6 and explaining the example. FIG. 5(a) shows a living body model obtained. FIG. 5(B) shows simulation of the movement of the obtained living body model which was partially cut.

DESCRIPTION OF THE PREFERRED EMBODIMENTS

Figure-Forming Composition

Figure 1:
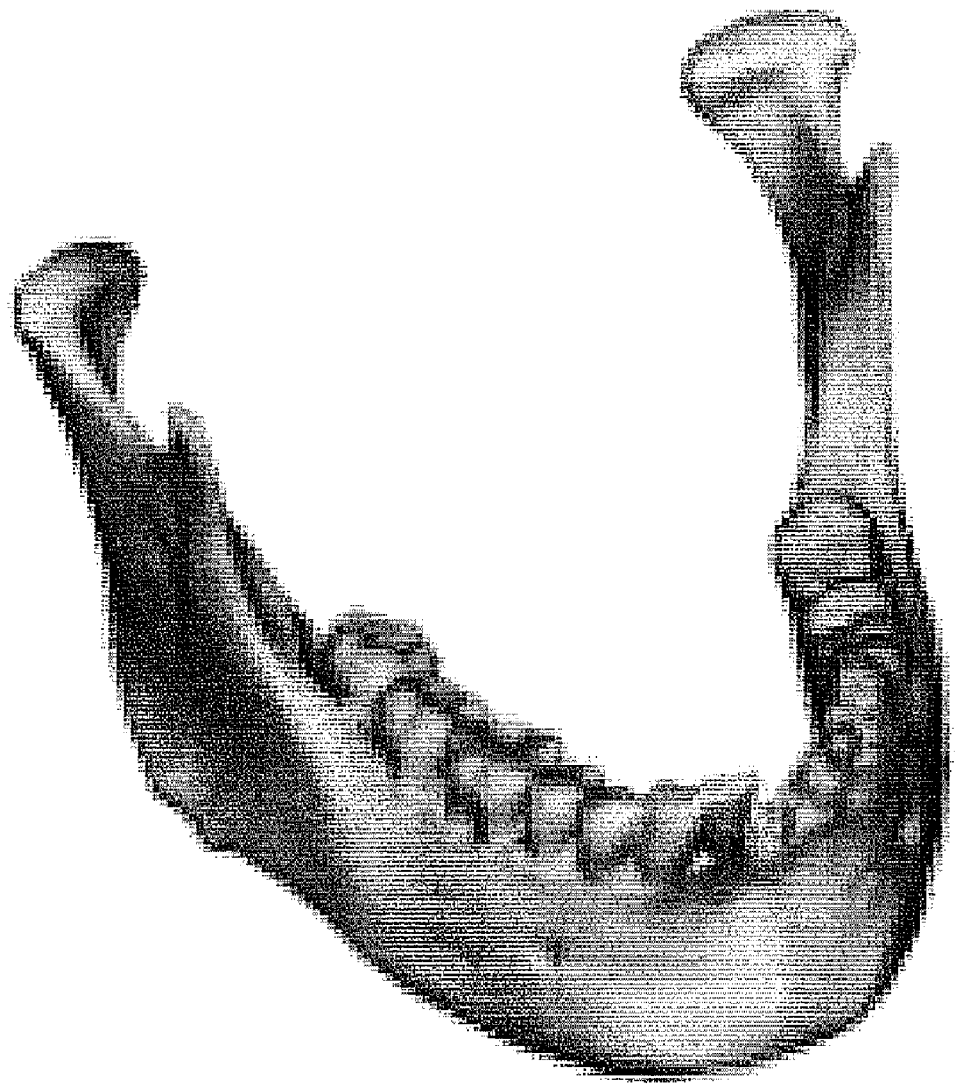
FIG. 1 is a figure showing the shape of an object formed in example 1.

The figure-forming composition according to the first aspect of the present invention is a figure-forming composition comprising a calcium-based material and a polyvinyl alcohol resin, wherein the polyvinyl alcohol resin is 2 to 8 weight parts when the total weight of the calcium-based material and the polyvinyl alcohol resin is 100 weight parts.

A preferred embodiment of the figure-forming composition according to the first aspect of the present invention is a figure-forming composition comprising a calcium-based material, a polyvinyl alcohol resin, and a hardening accelerator, wherein the hardening accelerator is one or more kinds of hardening accelerators selected from the group consisting of "dihydrate gypsum, alkali metal sulfate, alkaline earth metal sulfate, alkali metal chloride salt, alkaline earth metal chloride salt, inorganic acid ammonium salt, and alums", wherein the polyvinyl alcohol resin is 2 to 8 weight parts and the hardening accelerator is 0.1 to 5 weight parts when the total weight of the calcium-based material and the polyvinyl alcohol resin is 100 weight parts. It is preferred that the figure-forming composition according to this embodiment exclusively comprise calcium-based material, polyvinyl alcohol resin, and hardening accelerator.

As above explained, it is preferred that these figure-forming composition does not practically contain water except crystal water, and the one in powdered shaped is preferred. As far as figure-forming composition for building material is concerned, particle size of gypsum powder, which is raw material of the figure-forming composition, will not be a problem because gypsum powder is dissolved sufficiently by being mixed with water and the like. But, since the figure-forming composition of the present invention is not always intended to be in the form of slurry, the particle size of calcium-based material powder is preferred to be almost equalized. From this perspective, equal to or more than 50 weight parts of the molecule of the calcium-based material of the present invention should be located in the range of plus/minus 10% of the maximum distribution, according to a measurement of particle distribution based on JISR1619 (Testing method for size distribution of fine ceramic particles by liquid photosedimentation method). It is preferred that equal to more than 70 weight parts, more preferably equal to more than 85 weight parts, and further preferably equal to more than 95 weight parts thereof be located in the range of plus/minus 10% of the maximum distribution. This distribution can be achieved by repeatedly sorting out the ingredient powders.

A preferred example of calcium-based material of the present invention is gypsum. And examples of gypsum include α-type hemihydrate gypsum, β-type hemihydrate gypsum, or mixture of both. Among them, α-type hemihydrate gypsum is preferred. This is because, compared with β-type hemihydrate gypsum, α-type hemihydrate gypsum can achieve a kneaded state with little water, and hardening can be promoted. Hemihydrate gypsum having a small repose angle (repose angle is the maximum angle of inclination at which powders can form a stable slope) is preferred to be used, because the powders can be spread uniformly at the time of molding. From this perspective, the repose angle of hemihydrate gypsum (or figure-forming composition) is in the range of 30 to 45 degree, preferably 35 to 40 degree.

The polyvinyl alcohol resin of the present invention is not specifically restricted, and publicly known polyvinyl alcohol resin (polyvinyl alcohol $-[C(OH)HCH_2]_n-$) or polyvinyl alcohol resin having a functional group as appropriate) can be used as needed. As the polyvinyl alcohol resin, saponified material (which is produced by saponifying lower alcohol solution of polyvinyl acetate with saponifying catalyst such as alkali or acid, in general) or derivative therefor can be used. Also, as polyvinyl alcohol resin, monomer which copolymerized with vinyl acetate, and saponified material which is a copolymer with vinyl acetate can be used. The examples of monomer which copolymerized with vinyl acetate include: olefine such as ethylene, propylene, isobutylene, α-octene, α-dodecene, and α-octadecene, unsaturated acids such as acrylic acid, methacrylic acid, crotonic acid, maleic acid, maleic anhydride, and itaconic acid or the salt thereof or monoalkyl or dialkyl ester, nitrites such as acrylonitrile or meta acrylonitrile, amides such as acrylic amide, and methacrylamide, olefine sulfonic acid such as ethylene sulfonic acid, allyl sulfonic acid, and meta allyl sulfonic acid or the salt thereof, alkyl vinyl ethers, N-acrylic amide methyl trimethyl ammonium chloride, allyl trimethyl ammonium chloride, dimethyl diallyl ammonium chloride, dimethyl allyl vinyl ketone, N-vinyl pyrrolidone, vinyl chloride, vinylidene chloride, polyoxyalkylene (meta) allyl ether such as polyoxyethylene (meta) allyl ether and polyoxypropylene (meta) allyl ether, polyoxyalkylene (meta) acrylate such as polyoxyethylene (meta) acrylate and polyoxypropylene (meta) acrylate, polyoxyalkylene (meta) acrylic amide such as polyoxyethylene (meta) acrylic amide, and polyoxypropylene (meta) acrylic amide, polyoxyethylene (1-(meta) acrylic amide-1,1-dimethylpropyl) ester, polyoxyethylene vinyl ether, polyoxypropylene vinyl ether, polyoxyethylene allylamine, polyoxypropylene arylamine, polyoxyethylene vinyl amine, polyoxypropylene vinyl amine. Preferably, saponified material of homopolymer of the vinyl acetate, saponified substance of copolymer of vinyl acetate and ethylene, unsaturated acid or the salt thereof, alkyl ester and olefine sulfonic acid or the salt thereof are used.

The figure-forming composition of the present invention, different from building materials and the like, is not needed to be placed in a mold nor kneaded. So, saponification degree and average degree of polymerization of polyvinyl alcohol resin is not specifically restricted. On the other hand, since mechanical strength of a three-dimensional figure is not improved with less than 70 mol % of saponification degree, the saponification degree is preferred to be equal to or more than 70 mol %, and more preferably it is in the range of 80 to 99.5 mol %. If the average polymerization degree of polyvinyl alcohol resin is below $2\times10^2$, the viscosity of slurry becomes too low. In contrast, if the average polymerization degree of polyvinyl alcohol resin is over $3\times10^3$, the viscosity of slurry becomes too high, which makes it difficult to be dissolved in water. So, the range of polymerization degree is for example $2\times10^2$ to $3\times10^3$, and it may also be $5\times10^2$ to $2.5\times10^3$. It may also be, for example, $3\times10^3$ to $1\times10^4$, because the figure-forming composition of the present invention is not needed to be placed in a mold nor kneaded. Also, if the polymerization degree is low, when water is added to the figure-forming composition and make it in the form of slurry, gypsum particles are settled out therein. But the figure-forming composition of the present invention is not need to be in the form of slurry. Since it is preferred that the polymerization degree be low and be easily dissolved in a little amount of water, the polymerization degree is, for example, $5 \times 10$ to $1.9 \times 10^2$, and it may also be $1 \times 10^2$ to $1.5 \times 10^2$. The polymerization degree or molecular weight can be controlled by adjusting reaction time or conditions as appropriate based on publicly known method.

Concerning polyvinyl alcohol resin, saponification degree of complete saponification type is, for example, in the range of 90 to 99.5 mol % both inclusive. And more preferably the range is 98.5 to 99.5 mol % both inclusive. As for viscosity thereof, $1 \times 10$ to $2 \times 10$ mPa·s is preferred. The viscosity is preferred to be measured based on JIS standard (e.g. JIS K 7367).

Note that polyvinyl alcohol resin may be polyvinyl alcohol resin itself, and it may be the resin of the polyvinyl alcohol derivative introducing a functional group as appropriate. Also, the functional group may be partially introduced thereto. And the polyvinyl alcohol resin may be a mixture of several kinds of polyvinyl alcohol resin. The examples of the functional group include an acetoacetyl group, a silyl group, a quaternary ammonium base, a carboxylic acid group, an inorganic base of carboxylic acid, a sulfonic group, an inorganic base of the sulfonic acid, a ketone group, a mercapto group, and an amino group. One or more than one kind of the above functional groups may be included. Among them, an acetoacetyl group or a silyl group is preferred, and the most preferred one include an acetoacetyl group as a functional group. Note that all the hydroxyl groups (—OH) may be substituted with functional groups, 5 to 95% of the hydroxyl groups may be substituted with functional groups, and 10 to 20%, 70 to 90%, or 30 to 70% of the hydroxyl groups may be substituted with functional groups. In particular, polyvinyl alcohol resin having an acetoacetyl group forms chelate with a metal ion which is contained in hardening accelerator, thereby achieving a prescribed hardness with little amount of water in a short period. These functional groups can be introduced to polyvinyl alcohol resin obtained as appropriate, based on a general method of organic synthesis. The kind or ratio of functional groups introduced can also be controlled based on a general method of organic synthesis.

As demonstrated in the example below, the polyvinyl alcohol resin is mixed with the calcium-based material so that the polyvinyl alcohol resin is 2 to 8 weight parts per 100 weight parts of the total of the calcium-based material and the polyvinyl alcohol resin. As demonstrated in the example below, polyvinyl alcohol resin is preferred to be in the range of 3 to 7 weight parts. It may also be in the range of 3 to 6 weight parts, or 4 to 7 weight parts. It may further be in the range of 4 to 6 weight parts, or 4.5 to 5.5 weight parts. A suitable level of hardness can not be achieved with little amount of polyvinyl alcohol resin. On the other hand, if too much amount of polyvinyl alcohol resin is included, it is difficult to obtain three-dimensional structures which can stand autoclave sterilization.

The figure-forming composition of the present invention may include the polyvinyl alcohol resin which is separate from calcium-based material, or it may be a mixture of calcium-based material and polyvinyl alcohol resin. In both cases, the figure-forming composition is preferred to be in a powdered state, and the size of the powders are preferred to be in the range as above described.

The hardening accelerator of the present invention is one or more than one kind of hardening accelerator selected from a group consisting of: dihydrate gypsum, alkali metals sulfate, alkaline earth metal sulfate, alkaline metals chloride salt, alkaline earth metal chloride salt, inorganic acid ammonium salt, and alums. The examples of alkali metals sulfate include sodium sulfate and potassium sulfate. The examples of alkali earth metal sulfate include magnesium sulfate, calcium sulfate and barium sulfate. The examples of alkali metals chloride salt include lithium chloride, sodium chloride and potassium chloride. The examples of alkaline earth metal chloride salt include magnesium chloride and calcium chloride. The example of inorganic acid ammonium salt includes ammonium hydrochloride. The examples of alums include potassium alum such as aluminum potassium sulfate 12 water: $AlK(SO_4)_2 \cdot 12H_2O$, sodium alum such as $AlNa(SO_4)_2 \cdot 12H_2O$, ammonium alum such as $NH_4Al(SO_4)_2 \cdot 12H_2O$. Among them, one or more than one kind selected from a group consisting of magnesium sulfate, sodium chloride, sodium sulfate, and calcium sulfate can preferably be used. And, a mixture of dihydrate gypsum; and one kind or more than on kind selected from a group consisting of magnesium sulfate, sodium chloride, sodium sulfate, and calcium sulfate can preferably be used. Also, a hardening accelerator having metal salt is preferred, because it forms a chelate structure with polyvinyl alcohol having a predetermined functional group, and improves the hardness of three-dimensional figures or three-dimensional structures.

When the hardening accelerator is added to the mixture of calcium-based material and polyvinyl alcohol resin, 0.1 to 5 weight parts of the hardening accelerator is preferred to be added to 100 weight parts of the total of calcium-based material and polyvinyl alcohol resin. The amount of dihydrate gypsum as hardening accelerator is, for example, 0.5 to 5 weight parts. On the other hand, the amount of hardening accelerator contained not having dihydrate gypsum is, for example, 0.1 to 5 weight parts, preferably 0.1 to 3 weight parts, further preferably 0.3 to 2 weight parts, and more preferably 0.4 to 1.5 weight parts, per 100 weight parts of the total amount of hemihydrate gypsum and polyvinyl alcohol resin.

The hardening accelerator is preferred to be mixed with figure-forming composition according to a publicly-known method in the field of figure-forming composition. The figure-forming composition of the present invention may include known compositions other than the ones above described as far as it retains the function of the figure-forming composition of the present invention.

Method for Forming Three-Dimensional Figures

The final object of the present invention is to obtain gypsum hardening body such as three-dimensional living body models for surgical training. But before obtaining the three-dimensional living body models, three-dimensional models, including ones having insufficient hardness, are obtained. In the beginning, a method for forming three-dimensional figures is explained.

In the method for forming three-dimensional figures according to the second aspect of the present invention, basically, one of the above described figure-forming compositions which is in powdered state is used, when a three-dimensional figure is produced according to the rapid prototype process (the RP process). By using the above described figure-forming composition, even if a three-dimensional figure is formed by accumulating multiple layers to which a little amount of water (water, cross-linker solution, publicly known binder aqueous solution used for RP apparatus) was added, a three-dimensional figure having enough hardness to maintain a tentative form can be formed in a short period. It is also preferred that a unified three-dimensional figure be formed from adhesively joined layers each of which have certain level of hardness by being added with a small amount of water. The three-dimensional figure having the above characteristics can not be obtained by using the existing figure-forming composition as it is. But, by using the figure-forming composition of the present invention, a method for forming a three-dimensional figure according to this aspect can be obtained.

In particular, the method for forming three-dimensional figure according to the second aspect of the present invention is a method for forming a three-dimensional figure duplicating the shape of an object, the method comprising: a cross-sectional shape obtaining step (step A1) for obtaining information on the cross-sectional shape of each layer by dividing three-dimensional shape of the object into multiple layers; a first cross-sectional figure forming step (step A2-1) comprising the steps of: reading out information on the cross-sectional shape of a first layer from the information on the cross-sectional shape obtained in the cross-sectional shape obtaining step; and forming the first cross-sectional figure duplicating the cross-sectional shape by using a figure-forming composition based on the read out information; a second cross-sectional figure forming step (step A2-2) comprising the steps of: reading out information on the cross-sectional shape of a second layer from the information on the cross-sectional shape obtained in the cross-sectional shape obtaining step, the second layer being located on the upper layer of the first cross-sectional figure; and forming the second cross-sectional figure so as to be overlapped with the first cross-sectional figure, the second cross-sectional figure duplicating the cross-sectional shape from a figure-forming composition based on the read out information; a three-dimensional figure obtaining step (step A2-n) for obtaining the three-dimensional figure duplicating the shape of the object, wherein the three-dimensional figure obtaining step repeats, an upper layer cross-sectional figure forming step for forming an upper layer cross-sectional figure, in the same way as the second cross-sectional figure forming step, of: reading out information on the cross-sectional shape of the layer to be formed from the information on the cross-sectional shape obtained in the cross-sectional shape obtaining step; and forming the cross-sectional figure of the layer so as to be overlapped with the cross-sectional figure obtained in the former cross-sectional figure forming step, the cross-sectional figure of the layer duplicating the cross-sectional shape from a figure-forming composition based on the read out information, wherein at least one or more of the cross-sectional figure forming steps comprise: a figure-forming composition layer obtaining step for forming figure-forming composition layers by stratifying one of the powders of the figure-forming composition above described; and a water adding step for moistening a predetermined part of the figure-forming composition layer by adding water to the figure-forming composition layer based on information on the cross-sectional shape of the layer, the layer formed in the figure-forming composition layer obtaining step. Hereinafter, each step is explained.

A cross-sectional shape obtaining step (step A1) is a step for obtaining information on the cross-sectional shape of each layer by dividing three-dimensional shape of the object into multiple layers based on information on the three-dimensional shape of the object. A preferred embodiment of the method for forming three-dimensional figures according to the second aspect of the present invention is the above described method for forming three-dimensional figures, wherein the information on the cross-sectional shape of each layer comprises color identification information of each layer, and wherein water including coloring component is added based on the color identification information in the water adding step.

The method for forming three-dimensional figures according to the second aspect of the present invention can be easily performed by a publicly known apparatus used in, what is called, rapid prototype process, which is programmed to perform the steps of the method. In particular, the method is performed easily by using a computer which is programmed for rapid prototype process. This computer comprises an input/output part, a control part such as a CPU, a computing part, and a memory part. And it is connected with three-dimensional figure forming part for forming three-dimensional figures via an input/output part such as an interface. And the three-dimensional figure forming part comprises: a movable table for moving upward and downward to form a three-dimensional figure based on directions from the computer; a figure forming composition layer forming part for forming figure forming composition layer, by taking out figure forming composition powers from figure forming composition powder storing part in order to form figure forming composition layers on the movable table based on the orders from the computer; and a printing part for adding water or prescribed aqueous solution to the figure forming composition layer based on the orders from the computer.

In the cross-sectional shape obtaining step, it is preferred to obtain information concerning three-dimensional shape of an object, and then obtain images divided in cross-sectional shape composed of several layers of the three-dimensional shape. Also, the three-dimensional shape of implants and artificial bones can be obtained, for example, in the following way. In the first place, in order to obtain implants or artificial bones which fill defective sites, information on three-dimensional shape of the object may be obtained by computer simulating the shape of the bone of the object site so that the bones become in contrast. This is because a defective site generally has a counterpart whose shape is nearly in contrast with the defective site (for example, a right foot bone and a left hoot bone). Also, there are cases, such as manufacturing dental implants, that the shape of a diseased part itself is not suitable for duplicating. In this case, the shape of the object is drawn by 3DCG (three-dimensional computer graphics) based on the shapes of surrounding teeth and bones, and a computer obtains the information on the three-dimensional shape by inputting the 3DCG information, then information on each cross-sectional shape may be obtained by the computer based on the three-dimensional shape. In particular, when a signal from a pointing device is inputted in a CPU, the CPU reads out controlling program stored in the memory part such as CD-ROM or a hard disc based on the inputted signal. And the CPU scans X-ray figure stored in the memory part based on a direction from the controlling program, and a figure related to the three-dimensional shape is obtained by gathering a plurality of scanned two-dimensional figures. Note that since the X-ray photograph of bone or tooth part, and that of flesh part (or nervous part) are different in contrasting density, when the figure is obtained by scanning the X-ray photograph, an outline may be obtained from parts largely different in contrasting density. Also, patterning information of the bone part and the flesh part may be stored by obtaining the information, which is obtained by evaluating whether the contrasting density of the parts surrounded by the outline is in the range of predetermined value, or by comparing contrasting density of the part surrounded by the outline. Furthermore, when a figure concerning three-dimensional shape is obtained, the three-dimensional shape is, for example, sliced in the direction of Z-axis (the direction from the earth to the air), thereby obtaining cross sectional shape of each of a plurality of layers.

The thickness of the layers may be adjusted as appropriate according to input information from the pointing device and the like. It may also be controlled according to a preset value. If the thickness of the layer is too thick, an elaborate hardening body cannot be obtained, and there is a problem that the hardness for maintaining the shape cannot be achieved by adding water drops thereto by using devices such as printing mechanism. On the other hand, if the thickness of the layer is too thin, too many cross-sectional figures must be obtained, thereby causing a burden on the computer hardware resource, and too much time is required for forming a figure. From this perspective, the thickness of each layer is, for example, $1\times10$ μm to 5 mm. It may be $1\times10$ μm to 5 mm, or may be $1\times10^2$ μm to 1 mm. Note that the thickness of each layer is preferred to be uniform, but may not be uniform.

The first cross-sectional figure forming step (step A2-1) comprises the steps of: reading out information on the cross-sectional shape of a first layer from the information on the cross-sectional shape obtained in the cross-sectional shape obtaining step; and forming the first cross-sectional figure duplicating the cross-sectional shape by using a figure-forming composition based on the read out information.

The second cross-sectional figure forming step (step A2-2) comprises the steps of: reading out information on the cross-sectional shape of a second layer from the information on the cross-sectional shape obtained in the cross-sectional shape obtaining step, the second layer being located on the upper layer of the first cross-sectional figure; and forming the second cross-sectional figure so as to be overlapped with the first cross-sectional figure, the second cross-sectional figure duplicating the cross-sectional shape from a figure-forming composition based on the read out information.

Next, wherein the three-dimensional figure obtaining step repeats, an upper layer cross-sectional figure forming step for forming an upper layer cross-sectional figure, in the same way as the second cross-sectional figure forming step, reading out information on the cross-sectional shape of the layer to be formed from the information on the cross-sectional shape obtained in the cross-sectional shape obtaining step; and forming the cross-sectional figure of the layer so as to be overlapped with the cross-sectional figure obtained in the former cross-sectional figure forming step, the cross-sectional figure of the layer duplicating the cross-sectional shape from a figure-forming composition based on the read out information, A method for forming a three-dimensional figure duplicating a shape of an object, wherein at least one or more of the cross-sectional figure forming steps comprise: a figure-forming composition layer obtaining step for forming figure-forming composition layers by stratifying powders of the figure-forming composition above described; and a water adding step for moistening a predetermined part of the figure-forming composition layer by adding water to the figure-forming composition layer based on information on the cross-sectional shape of the layer, the layer formed in the figure-forming composition layer obtaining step.

Hereinafter, examples of each cross-sectional figure forming step is explained. In each cross-sectional figure forming step, the CPU receive a direction from the controlling program, and read out information on the thickness of a figure-forming composition layer, then outputs the information from the input/output device. The three-dimensional figure forming part having received the information on the thickness shifts the movable table downward following an order from the computer. The downward shift distance corresponds to the thickness of the figure-forming composition layer. The information on the downward shift distance is also outputted from the computer. And the movable table moves based on the shift distance information. Note that if the thickness of each layer is the same, the memory part of the three-dimensional figure forming part stores this information, and may use the same information in forming each layer.

Next, the CPU receives the direction from the controlling program, and, for example, reads out information on the thickness of the figure-forming composition layer, computes the amount of figure-forming composition suitable for forming the figure-forming composition layer, then outputs the information of the amount from the input/output part. This amount may be fixed, and having transmitted to the three-dimensional figure forming part, it may be stored in the store part of the three-dimensional figure forming part, and the same information may be used for forming each layer. The three-dimensional figure forming part which have received information on this figure-forming composition layer, based on the direction from the computer, makes the figure-forming composition layer forming part take out figure-forming composition powder from the figure-forming composition powder storing part, then releases the powder on the table. The three-dimensional figure forming part may control the figure-forming composition layer forming part to uniform the figure-forming composition layer by moving a squeegee or a spatula. In this way, the figure-forming composition layer is formed on the movable table (if already a layer is formed, another layer will be formed on a figure-forming composition layer formerly formed).

Next, having received a direction from the controlling program, the CPU reads out information on the cross-sectional shape of each layer or information on pattering, and outputs the information from the input/output part. The three-dimensional figure forming part, based on a direction from the computer, activates a printing part, and adds water or predetermined aqueous solution (water, cross-linker solution, binder aqueous solution for rapid prototyping) to the figure-forming composition layer. This mechanism can be easily achieved by using a controlling mechanism of a well known printer. Note that the conditions such as the composition, the density, and the amount of water or aqueous solution to be added can be adjusted as appropriate. For example, information on these conditions is inputted from the pointing device, and the inputted information is stored in the store part of the computer. Based on the information on these conditions, the CPU reads out necessary information and makes the computing part to perform computing, and controls the operation of the printing part. The printing part uses ordinary printing techniques except adding water instead of ink. The liquid binder material added to the figure-forming composition layer may be organic or inorganic. Typical organic binder material used is a ceramic precursor such as polymer resin or polycarbosilazane. Inorganic binder is used when a binder is mixed with the final material, in which silica is generally used.

Ordinarily, in the step of forming each layer, the amount of water which is more than the amount necessary for accelerating hydration reaction is repeatedly added and dried. But, in the method for forming three-dimensional figure of the present invention (the method for forming hardening material of the present invention), the hydration reaction of gypsum is not need to be completed in the above step. So, in each cross sectional figure-forming step, for example, when the amount water necessary for hydrating the figure-forming composition completely is assumed to be 100 weight parts, the amount of water to be added may be, for example, 1 to 50 weight parts, 1 to 20 weight parts, 2 to 10 weight parts, or 3 to 5 weight parts. This little amount of water is not sufficient for completing the hydration reaction of gypsum. However, in the present invention, with this little amount of water, layers with hardness which is enough for maintaining least hardness can be obtained rapidly. Also, since the amount of water is little, the water can be prevented from spreading to unintended part, thereby obtaining layers having desired cross-sectional structures. In particular, in case of obtaining a cross-sectional structure which has more than two kinds of patterning, it is necessary for preventing two kinds of water or aqueous solution from being mixed. With little amount of water to be added, these two kinds of water or aqueous solution can be prevented from being mixed.

Having repeatedly performed the cross-sectional figure forming step, it is preferred to dry the resultant layered product until it has a certain level of hardness. The drying may be performed in low humidity high temperature atmosphere (for example humidity 0 to 10%, temperature 50 to $2\times10^{2\circ}$ C.), but may be performed at ordinary temperatures and pressures. The drying time at an ordinary temperature and pressure is preferred to be adjusted as appropriate, according to the size, the moisture percentage, and the thickness of each layer of the resultant three-dimensional figure. The examples of the drying time include 1 minute to 1 hour, 5 minutes to $3\times10$ minutes, and 5 minutes to $2\times10$ minutes. Namely, in using the rapid prototype process in the present invention, figure-forming composition containing a large amount of polyvinyl alcohol resin is used, so a figure-forming composition having relatively high level of hardness could be obtained. And in this step, the figure-forming composition need not contain enough water, so drying time can be remarkably shortened. Then, after drying the layered product, a three-dimensional figure duplicating the shape of an object can be obtained.

It is highly likely that the three-dimensional figure obtained in the above way contains gypsum whose hydration reaction does not proceeded. So, the hardness thereof is assumed to be low compared to that of three-dimensional figure whose hydration reaction is preceded. However, by patterning layers with a little amount of water, water can be prevented from spreading to unintended parts, thereby preventing the unintended parts from being hardened. So, this method for forming three-dimensional figure is useful for forming three-dimensional figure having a sophisticated shape in a short period. On the other hand, the three-dimensional figure obtained in the above way has a sophisticated shape, but it is assumed that the hardness thereof is low because the hydration reaction is not sufficiently preceded. In order to obtain enough hardness, it is preferred that hydration reaction be proceeded according to the method for forming hardening object described later.

The Method for Forming Three Dimensional Structures

As above described, the method for forming three-dimensional structures according to the third aspect of the present invention is the method for obtaining hardening body having enough hardness basically by the following procedures. The resultant three-dimensional figure obtained in the above each step is soaked into water or aqueous solution, thereby accelerating hydration of gypsum. And then the resultant figure is dried.

Namely, the method for forming a three-dimensional structure according to the third aspect of the present invention relates to the method comprising: a gypsum powder removing step (step B1) for removing unconsolidated figure-forming composition powder from the three-dimensional figure basically obtained by one of the method for forming a three-dimensional figure above described; a water adding step (step B2) for adding water to the three-dimensional figure whose unconsolidated powders were removed in the gypsum powder removing step; and a drying step (step B3) for drying the three-dimensional figure to which water was added in the water adding step. Hereinafter, each step is explained.

Gypsum powder removing step (step B1) is a step for removing powders of unhardened figure-forming composition from the three-dimensional figure. In this step, for example, unhardened gypsum powders are blown off by an airbrush. The amount of airflow, the shape of the airbrush, and the like may be adjusted as appropriate, and a well known airbrush can be used. The time required for the gypsum powder removing step is also adjusted as appropriate. The specific example is 5 minutes to 1 hour, and 10 minutes to 30 minutes is preferred.

Water adding step (step B2) is a step for adding water to the three-dimensional figure whose powders are removed in the gypsum powder removing step. In this water adding step, enough water for accelerating hydration reaction of gypsum is preferred to be added to a three-dimensional figure. In this water adding step, three-dimensional figure is soaked in water or predetermined aqueous solution. In this process, since unnecessary powders are removed in the former gypsum powder removing step, figure-forming composition powders unnecessary for forming the shape of the three-dimensional figure can be prevented from sticking to the three-dimensional figure.

A preferred embodiment of the method for forming three-dimensional structures according to the third aspect of the present invention includes the water adding step (step B2) which comprises: an atomizing step (step B2-1) for attaching water on the surface of the three-dimensional figure by misting water or by exposing the three-dimensional figure to high humidity atmosphere, the three-dimensional figure being removed unconsolidated powders therefrom in the gypsum powder removing step; and a soaking step (step B2-2) for soaking the three-dimensional figure in water after the atomizing step.

There is a problem that the shape of three-dimensional figure is deformed if the resultant three-dimensional figure is soaked in water suddenly. Considering this problem, the following procedures are taken in this embodiment of the method for forming three-dimensional structure. Firstly, water is added on the surface (preferably on all over the surface) of the resultant three-dimensional figure, thereby accelerating the hardening reaction, at least, on the surface thereof through hydration reaction of gypsum (preferably followed by drying the figure) and preventing the figure from being deformed. Then, the hardening reaction is further accelerated by soaking the figure in water. In the atomizing step, for example, water or predetermined aqueous solution (preferably water, cross-linker solution, or binder aqueous solution) is sprayed on the surface of the three-dimensional figure by using a known spray. Or water is added on the surface of the three-dimensional figure by placing the three-dimensional figure in high humidity atmosphere. Then, having sprayed water, the figure is dried, and then soaked in water. The figure may be dried in low humidity high temperature atmosphere (for example humidity 0 to 10%, temperature 50 to $2\times10^{2\circ}$ C.), but may be dried at an ordinary temperature and pressure. The drying time at an ordinary temperature and pressure is preferred to be adjusted according to the size, the moisture percentage, and the thickness of each layer of the resultant three-dimensional figure, as appropriate. The examples of the drying time include $1\times10$ minutes to 2 hours, 15 minutes to 1 hour, and $2\times10$ minutes to $4\times10$ minutes. In the soaking step, the three-dimensional figure is soaked in sufficient water or aqueous solution. The soaking time may be adjusted as appropriate according to the size of the three-dimensional figure. The examples of the soaking time include $1\times10$ minutes to 2 hours, 15 minutes to 1 hour, and $2\times10$ minutes to $4\times10$ minutes.

A preferred embodiment of the method for forming three-dimensional structure according to the third aspect of the present invention is the above described method for forming three-dimensional structure comprising the water adding step (step B2) which comprises: (1) an atomizing step for attaching water on the surface of the three-dimensional figure by misting water or by exposing the three-dimensional figure to high humidity atmosphere, the three-dimensional figure being removed unconsolidated powders therefrom in the gypsum powder removing step, and a soaking step for soaking the three-dimensional figure in cross-linker solution after the atomizing step; (2) an atomizing step for attaching cross-linker solution on the surface of the three-dimensional figure by misting cross-linker solution or by exposing the three-dimensional figure to high humidity atmosphere of cross-linker solution, the three-dimensional figure being removed unconsolidated powders therefrom in the gypsum powder removing step, and a soaking step for soaking the three-dimensional figure in cross-linker solution after the atomizing step; or (3) an atomizing step for attaching water on the surface of the three-dimensional figure by misting water or by exposing the three-dimensional figure to high humidity atmosphere, the three-dimensional figure being removed unconsolidated powders therefrom in the gypsum powder removing step, and a soaking step for soaking the three-dimensional figure in water and then in cross-linker solution after the atomizing step. In particular, step (1) or (3) is preferred to be used for figure-forming composition containing acetoacetyl group modified polyvinyl alcohol resin. This is because, in view of hardness or uniformity of the three-dimensional structure, it is preferred to promote bridging reaction with a cross-linker, after having developed chelate structures with water.

In this way, by adding a cross-linker such as cross-linker solution, cross-linking reaction proceeds in the three-dimensional figure, and a three-dimensional structure having enough hardness can be obtained. The atomizing step and the soaking step are performed in the same way as above explained. The density of cross-linker solution is adjusted as appropriate according to the kind of polyvinyl alcohol resin used and the hardness of the hardening body to be obtained. The concentration of cross-linker solution is specifically $1\times10^{-2}$ to $2\times10$ volume %, preferably $1\times10^{-1}$ to $1.5\times10$ volume %. As cross-linker solution, in place of or together with amine cross-linker solution such as ethylenediamine or diethanolamine, the following materials can be used as appropriate: aldehyde compound such as formaldehyde or glyoxal; methylol compound such as melamine-formaldehyde condensate or urea-formaldehyde condensate; boron-containing compound such as boracic acid or borax; isocyanate compound such as 2,4-tolylene diisocyanate, 2,6-tolylene diisocyanate, m-phenylene diisocyanate, p-phenylene diisocyanate or 4,4-diphenylmethane diisocyanate; or silane coupling agent. Among them, as a cross-linker, amine cross-linker solution such as ethylenediamine or diethanolamine is preferred. In particular, as demonstrated in the example described later, one or both of ethylenediamine and diethanolamine is more preferred.

The drying step (step B3) is a step for drying the three-dimensional figure which is added water in the water adding step. The drying may be performed in low humidity high temperature atmosphere (for example, humidity 0 to 10%, temperature 50 to $2\times10^{2\circ}$ C.), but may be performed at an ordinary temperature and pressure. The drying time at an ordinary temperature and pressure is preferred to be adjusted according to the size, the moisture percentage, and the thickness of each layer of the resultant three-dimensional figure, as appropriate. The examples of the drying time include 1 hour to 4 days, 4 hours to 3 days, and 6 hours to 2 days.

The resultant three-dimensional structure has a sophisticated shape, because it can be obtained by enhancing the hardness thereof based on three-dimensional figure having a sophisticated shape. Furthermore, this three-dimensional structure basically does not contain wax, so there are no problems such as deformation of the structure and elution of wax component even if high temperature processing is performed on the structure. So, the three-dimensional structure can be sterilized in high temperature, and be brought in an operating room. Furthermore, this three-dimensional structure can be obtained as a sophisticated hardened body having substantially uniform hardness, because hydration reaction thereof has proceeded. So, it can be effectively used as a living body model for surgical training. Furthermore, a preferred embodiment of the three-dimensional structure of the present invention is, for example, as follows. Bone or tooth part is colored in white or whitish color, flesh part is colored in reddish color, and they are colored not only on the surface but inside the parts. As a result, they can be used for surgical training or surgical planning with more realistic sense compared to the conventional ones.

Three-Dimensional Structure

A three-dimensional living body model according to the fourth aspect of the present invention relates to a three-dimensional structure having a shape of a part including patient's bones or teeth. In particular, the three-dimensional structure according to the fourth aspect of the present invention relates to a three-dimensional structure of parts including patients' bones or teeth which is formed by one of the above described methods for forming three-dimensional structures, wherein the shape of the above described object is that of a part including patients' bones or teeth. In this way, custom made three-dimensional living body models, implants, artificial bones, or the like can easily be formed without producing expensive devices such as molds. And, since the resultant three-dimensional living body model duplicates the part including patient's bones and teeth, lines along which a bone is cut can be easily designed, or simulation for moving a bone can easily be performed. Also, a simulation for embedding implants or plates can easily be performed. Doctors and the like can actually see the three-dimensional living body models, which develop their understanding of surgical sites before actual surgeries are performed. Also, since doctors and the like can explain specific operational sequence to patients before operations, patients can understand the operational sequence which makes them feel secure. Furthermore, existing models including wax component and the like can not be sterilized in autoclave or in high temperature, so they can not be brought in operating rooms. But since the preferred embodiment of three-dimensional living body model of the present invention does not include wax component, it can be sterilized in autoclave or in high temperature, and can be brought in operating rooms. This makes doctors and the like remind of simulated operations previously preformed. Since the objects to be embedded in a living body such as implants or artificial bones obtained in the above way have desirable shapes, they can be preferably used in dentistry or surgical treatment. Namely, the present invention can provide a method for treating tooth or bone related diseases by embedding implants or artificial bones, which are formed in the above way, in diseased sites. In particular, when a part of a bone is defected in an accident, the shape of the part to be duplicated is presumed from the symmetry part thereof, and based on the presumed shape, a three-dimensional artificial bone is obtained which is embedded in the defected site. Also, in producing and embedding dental implants, by producing living body models from which implant embedding parts are removed, and also by producing implants or implant models, patients can have actual images of the surgery, which makes them satisfied, and doctors can easily confirm specific images of surgeries.

EXAMPLE 1

The present invention is explained in examples set forth hereinafter. The present invention, however, is not specifically limited to the examples, and various applications can be made based on the common general technical knowledge of the person skilled in the art.

The following materials were used as raw materials: Calcined gypsum as hemihydrate gypsum produced by San-Esu Gypsum Co., Ltd.; polyvinyl alcohol (PVA) produced by Noppon Gousei Co., Ltd.; dihydrate gypsum produced by San-Esu Gypsum Co., Ltd.; potassium sulfate (first grade) produced by Wako Pure Chemical Industries Ltd.; sodium chloride (first grade) produced by Wako Pure Chemical Industries Ltd.

In this example, 95 weight parts of hemihydrate gypsum and 5 weight parts of PVAZ-100 produced by Nippon Gousei Co., Ltd. was used as figure-forming composition, and 0.5 weight parts of dihydrate gypsum was used as hardening accelerator. The figure-forming composition was powder state, and was sifted for uniform particle size.

A three-dimensional figure was formed form the figure-forming composition by a RP apparatus produced by Z-Co-operation, to which a predetermined processing direction is inputted. The steps for forming three-dimensional figures disclosed in this specification, which are different form those disclosed in the manual of the PR apparatus, were applied. FIG. 1 is a figure showing the shape of an object formed in example 1. As shown in FIG. 1, in this example, a three-dimensional figure and a three-dimensional structure having a shape of lower jaw were produced. ZB56 color binder was used to form the cross-sectional figure of a layer duplicating the cross-sectional shape from figure-forming composition so as to be overlapped with the cross-sectional figure obtained in the former step. The resultant three-dimensional figure was dried for 10 minutes in room temperature, and then it was taken out. In general, it takes about 2 to 6 hours to dry three-dimensional figure. So, this drying time is considered to be quite short.

Having dried the three-dimensional figure, powders were removed from it by using an airbrush for 20 minutes. And then, water was sprayed on it, and it was dried for 30 minutes at room temperature. After that, it was soaked in water for 30 minutes. Finally, it was taken out of water, dried for 12 hours at room temperature, and a three-dimensional structure was obtained. In this process, it was not soaked in wax and the like.

The three-dimensional figure and a three-dimensional structure obtained in the example was evaluated in terms of hardness at the time when the three-dimensional figure was taken out, gloss of the surface of the three-dimensional structure, machinability, hardness after steam sterilization. The hardness at the time when the three-dimensional figure was taken out was rated as follows: (◯); no deformation was seen when three-dimensional figure was taken out after it was dried; (Δ): little deformation was seen; (x): deformation was seen. The gloss of the surface thereof was evaluated by visual inspection. The machinability was evaluated by cutting the resultant three-dimensional structure with surgical knife and considering if the actual feeling is close to that of a bone. The hardness after steam sterilization was evaluated if the hardness of the three-dimensional figure is maintained after an autoclave processing at 115° C. for 30 minutes.

The resultant three-dimensional figure and the three-dimensional structure were excellent in all aspects (i.e. (◯) for the hardness when the three-dimensional figure was taken out, the hardness after steam sterilization, the gloss of the surface thereof, and the machinability thereof).

EXAMPLE 2

Autoclave Test

This example was performed to examine the tolerance of the three-dimensional figure against autoclave processing, and the preferred relationship between PVA and cross-linking treatment. For example, EDA 5% means: having sprayed water on the surface of a dried three-dimensional figure and dried the figure, soaking the dried three-dimensional figure in 5 volume % aqueous solution of ethylenediamine. The evaluation of the autoclave tolerance was as follows: (◯): a three-dimensional structure (in this example, a living body model of an upper jaw was produced) could be taken out from autoclave apparatus after autoclave processing was performed at 115° C. for 30 minutes and then left until the temperature inside the autoclave became 60° C.; (x): the three-dimensional structure could not be taken out from the autoclave apparatus under the condition above described. The results are shown in table 1. In the table, "-" means that test was not performed. The kinds of PVA are the product numbers of PVA produced by Nippon Gousei Co., Ltd.

TABLE 1

Results of Autoclave Tests

| Gypsum | PVA | Content of PVA [%] | Only Water | EDA 5% | EDA 10% | EDA 20% | DEA 5% | DEA 10% | DEA 20% | Wax |
|---|---|---|---|---|---|---|---|---|---|---|
| Made by San-Esu Gypsum Co., Ltd. | Z-100 | 5 | ◯ | ◯ | ◯ | X | ◯ | ◯ | ◯ | — |
| | AL-06R | 5 | ◯ | ◯ | ◯ | X | ◯ | ◯ | ◯ | — |
| | NM-11 | 5 | ◯ | ◯ | ◯ | X | ◯ | ◯ | ◯ | — |
| | K-210 | 5 | ◯ | ◯ | ◯ | X | ◯ | ◯ | ◯ | — |
| | GL-05S | 5 | ◯ | ◯ | ◯ | X | ◯ | X | X | — |
| | | 0.6 | ◯ | — | — | — | — | — | — | — |

TABLE 1-continued

Results of Autoclave Tests

| | | | | Soaking material | | | | | | |
|---|---|---|---|---|---|---|---|---|---|---|
| Gypsum | PVA | Content of PVA [%] | Only Water | EDA 5% | EDA 10% | EDA 20% | DEA 5% | DEA 10% | DEA 20% | Wax |
| | | 2 | ○ | — | — | — | — | — | — | — |
| | | 10 | Δ | — | — | — | — | — | — | — |
| ZP102 | Unknown | Unknown | X | — | — | — | — | — | — | X |
| ZP130 | Unknown | Unknown | X | — | — | — | — | — | — | X |

It can be seen from the table 1 that preferred three-dimensional structures can not be obtained if the concentration of EDA is too high.

EXAMPLE 3

Crack Test

Figure 2:
FIG. 2 is a figure of 3D CG image for forming a three-dimensional structure of a thigh bone.
Figure 3:
FIG. 3 is a photograph, in place of a diagram, showing the evaluation of machinability of a three-dimensional structure.

In order to examine if the machinability is similar to that of bones, crack test was performed. A living body model of a thigh bone was produced, and a test piece was made from the living body model (three-dimensional structure). Four nails (diameter 3.2 mm) were driven in the test piece in a row, and examined if cracks appear by visual inspection. FIG. 2 is a figure of 3D CC image for forming a three-dimensional structure of a thigh bone. Namely, in this example, cross-sectional views of each layer were obtained based on the three-dimensional structure of the object shown in the FIG. 2. And based on the resultant cross-sectional views, three-dimensional figure was formed by duplicating the shape of the thigh bone shown in FIG. 2. In this way, a three-dimensional structure was produced. The results were rated as follows: (○): cracks did not appear; (x): cracks did appear. The results are shown in table 2. In addition, machinability test on the resultant three-dimensional structure was also performed. FIG. 3 is a photograph, in place of a diagram, showing the evaluation of machinability of a three-dimensional structure. When the machinability was evaluated, the same results as the former example were obtained.

TABLE 2

Results of Crack Tests

| | | | | Soaking material | | | | | | |
|---|---|---|---|---|---|---|---|---|---|---|
| Gypsum | PVA | Content of PVA [%] | Only Water | EDA 5% | EDA 10% | EDA 20% | DEA 5% | DEA 10% | DEA 20% | wax |
| Made by San-Esu Gypsum Co., Ltd. | Z-100 | 5 | ○ | ○ | ○ | ○ | ○ | ○ | ○ | — |
| | AL-06R | 5 | ○ | ○ | ○ | ○ | ○ | ○ | ○ | — |
| | NM-11 | 5 | ○ | ○ | ○ | ○ | ○ | ○ | ○ | — |
| | K-210 | 5 | ○ | ○ | ○ | ○ | ○ | ○ | ○ | — |
| | GL-05S | 5 | ○ | ○ | ○ | ○ | ○ | ○ | ○ | — |
| | | 0.6 | ○ | — | — | — | — | — | — | — |
| | | 2 | ○ | — | — | — | — | — | — | — |
| | | 10 | ○ | — | — | — | — | — | — | — |
| ZP102 | Unknown | Unknown | — | — | — | — | — | — | — | X |
| ZP130 | Unknown | Unknown | — | — | — | — | — | — | — | X |

EXAMPLE 4

Bending Strength Test

Next, bending strength was measured. The measurement was performed based on JISR1609. The results are shown in table 3. In the table, numbers are expressed by MPa. (*) in the table shows that measurement could not be performed because a test piece was broken in the soaking step.

TABLE 3

Results of Bending Strength Tests

| | | | | Soaking material | | | | | | |
|---|---|---|---|---|---|---|---|---|---|---|
| Gypsum | PVA | Content of PVA [%] | Only Water | EDA 5% | EDA 10% | EDA 20% | DEA 5% | DEA 10% | DEA 20% | wax |
| Made by San-Esu | Z-100 | 5 | 7 | 8.28 | 11.91 | 8.65 | 6.35 | 5.45 | 5.27 | — |
| | AL-06R | 5 | 9.78 | 10.63 | 13.47 | 7.75 | 5.84 | 6.52 | 5.69 | — |

TABLE 3-continued

Results of Bending Strength Tests

| | | | | Soaking material | | | | | | |
|---|---|---|---|---|---|---|---|---|---|---|
| Gypsum | PVA | Content of PVA [%] | Only Water | EDA 5% | EDA 10% | EDA 20% | DEA 5% | DEA 10% | DEA 20% | wax |
| Gypsum Co., Ltd. | NM-11 | 5 | 1.42 | * | * | * | 5.69 | 5.06 | 1.36 | — |
| | K-210 | 5 | 10.61 | 8.2 | 9.8 | 6.88 | 6.12 | 5.09 | 4.63 | — |
| | GL-05S | 5 | 5.86 | 5.36 | 5.24 | 4.83 | 3.14 | 2.6 | 4.31 | — |
| | | 0.6 | 4.5 | — | — | — | — | — | — | — |
| | | 2 | 4.7 | — | — | — | — | — | — | — |
| | | 10 | 3.65 | — | — | — | — | — | — | — |
| ZP102 | Unknown | Unknown | 4 | — | — | — | — | — | — | X |
| ZP130 | Unknown | Unknown | 8.63 | — | — | — | — | — | — | X |

EXAMPLE 5

FIG. 4 shows figures for explaining three-dimensional structures of a join part produced in example 5. FIG. 4(a) is a 3D CG image of an object to be obtained. FIG. 4(b) is a photograph, in place of a diagram, showing three-dimensional structures obtained. As shown in FIG. 4, this three-dimensional structure (1) includes: a living body part (2) for including bones and the like; and a base (3) for supporting the living body part. As shown in the FIG. 4, in the present invention, a sophisticated three-dimensional structure can be produced in a short period. Such a model promotes better understanding for patients. Also, implants or artificial bones having suitable shapes can be produced.

EXAMPLE 6

FIG. 5 shows photographs, in place of a diagram, showing a living body model formed in example 6, and explaining the example. FIG. 5(a) shows a living body model obtained. FIG. 5(B) shows simulation of the movement of the obtained living body model which was partially cut. As shown in FIG. 5, state of each bone tissue being machined and the like can easily be comprehended by the three-dimensional model of the present invention.

The figure-forming composition of the present invention, the same as the ordinary figure-forming composition, can be used as building materials and the like. In addition, it can preferably be used, for example, for three-dimensional models such as three-dimensional living body models, implants, artificial bones, or the like.

The method for forming three-dimensional figure of the present invention can be used for obtaining a three-dimensional figure of the present invention. And, the method for forming three-dimensional figure of the present invention is useful for forming three-dimensional figures which have sophisticated shapes in a short period. This three-dimensional figure, for example, may be used, as it is, as a figure having a predetermined shape. On the other hand, although the three-dimensional figure obtained in the above way has a sophisticated shape, the hardness thereof is assumed to be low because the hydration reaction has not proceeded sufficiently. So, the three-dimensional figure of the present invention can be used, for example, for forming hardening material whose hydration reaction has proceeded sufficiently.

The method for forming three-dimensional structure of the present invention can be used, for example, for obtaining three-dimensional structures such as living body models. The living body model can preferably be used in the field of medical equipment industry.

The three-dimensional structure of the present invention can be preferably used in the field of medical equipment industry, as custom made living body models, implants, artificial bones, and the like.

What is claimed is:

1. A method for forming a three-dimensional structure, the method comprising: a three-dimensional figure forming step for duplicating a shape of an object; and a three-dimensional structure obtaining step for obtaining a three-dimensional structure by using the three-dimensional figure formed in the three-dimensional figure forming step, the three-dimensional figure forming step comprising:

a cross-sectional shape obtaining step for obtaining information on the cross-sectional shape of each layer by dividing three-dimensional shape of the object into multiple layers;

a first cross-sectional figure forming step comprising the steps of: reading out information on the cross-sectional shape of a first layer from the information on the cross-sectional shape obtained in the cross-sectional shape obtaining step; and forming the first cross-sectional figure duplicating the cross-sectional shape by using a figure-forming composition based on the read out information;

a second cross-sectional figure forming step comprising the steps of: reading out information on the cross-sectional shape of a second layer from the information on the cross-sectional shape obtained in the cross-sectional shape obtaining step, the second layer being located on the upper layer of the first cross-sectional figure; and forming the second cross-sectional figure so as to be overlapped with the first cross-sectional figure, the second cross-sectional figure duplicating the cross-sectional shape from a figure-forming composition based on the read out information; and a three-dimensional figure obtaining step for obtaining the three-dimensional figure duplicating the shape of the object, wherein the three-dimensional figure obtaining step repeats, an upper layer cross-sectional figure forming step for forming an upper layer cross-sectional figure, in the same way as the second cross-sectional figure forming step, reading out information on the cross-sectional shape of the layer to be formed from the information on the cross-sectional shape obtained in the cross-sectional shape obtaining step; and forming the cross-sectional figure of the layer so as to be overlapped with the cross-sectional figure obtained in the former cross-sectional figure forming step, the cross-sectional figure of the layer duplicating the cross-sectional shape from a figure-forming composition based on the read out information, wherein at least one or more of the cross-sectional figure forming steps comprise:

a figure-forming composition layer obtaining step for forming figure-forming composition layers by stratifying powders of the figure-forming composition; and a water adding step for moistening a predetermined part of the figure-forming composition layer by adding water to the figure-forming composition layer based on information on the cross-sectional shape of the layer, the layer formed in the figure-forming composition layer obtaining step, wherein the figure-forming composition comprises a calcium-based material and a polyvinyl alcohol resin, wherein the polyvinyl alcohol resin is 2 to 8 weight parts when the total weight of the calcium-based material and the polyvinyl alcohol resin is 100 weight parts, the three-dimensional structure obtaining step by using the three-dimensional figure comprising:

a powder removing step for removing unconsolidated figure-forming composition powder from the three-dimensional figure obtained in the three-dimensional figure forming step;

a water adding step for adding water to the three-dimensional figure whose unconsolidated powders was removed in the powder removing step; and a drying step for drying the three-dimensional figure to which water was added in the water adding step, wherein the water adding step after the powder removing step comprises:

an atomizing step for attaching water on the surface of the three-dimensional figure by misting water or by exposing the three-dimensional figure to high humidity atmosphere, the three-dimensional figure being removed unconsolidated powders therefrom in the powder removing step; and a soaking step for soaking the three-dimensional figure in water or aqueous solution after the atomizing step.

2. The method for forming a three-dimensional structure as claimed in claim 1, wherein the water adding step after the powder removing step comprises:

an atomizing step for attaching water on the surface of the three-dimensional figure by misting water or by exposing the three-dimensional figure to high humidity atmosphere, the three-dimensional figure being removed unconsolidated powders therefrom in the powder removing step, and a soaking step for soaking the three-dimensional figure in cross-linker solution after the atomizing step.

3. The method for forming a three-dimensional structure as claimed in claim 2, wherein the cross-linker comprises one or both of ethylenediamine and diethanolamine.

4. The method for forming a three-dimensional structure as claimed in claim 1, wherein the figure-forming composition further comprises dihydrate gypsum, and wherein the calcium-based material is hemihydrate gypsum.

5. The method for forming a three-dimensional structure as claimed in claim 1, wherein the polyvinyl alcohol resin is 3 to 7 weight parts.

6. The method for forming a three-dimensional structure as claimed in claim 1, wherein the polyvinyl alcohol resin is 4 to 6 weight parts.

7. The method for forming a three-dimensional structure as claimed in claim 1, wherein the water adding step after the powder removing step comprises:

an atomizing step for attaching cross-linker solution on the surface of the three-dimensional figure by misting cross-linker solution or by exposing the three-dimensional figure to high humidity atmosphere of cross-linker solution, the three-dimensional figure being removed unconsolidated powders therefrom in the powder removing step, and a soaking step for soaking the three-dimensional figure in water or cross-linker solution after the atomizing step.

8. The method for forming a three-dimensional structure as claimed in claim 1, wherein the water adding step after the powder removing step comprises:

an atomizing step for attaching water on the surface of the three-dimensional figure by misting water or by exposing the three-dimensional figure to high humidity atmosphere, the three-dimensional figure being removed unconsolidated powders therefrom in the powder removing step, and a soaking step for soaking the three-dimensional figure in water and then in cross-linker solution after the atomizing step.

* * * * *